(12) United States Patent
Kim et al.

(10) Patent No.: US 7,514,227 B2
(45) Date of Patent: Apr. 7, 2009

(54) ANTI-HUMAN MITOCHONDRIAL ADENYLATE KINASE ISOZYME ANTIBODY, DIAGNOSTIC FORMULATION AND DIAGNOSTIC KIT FOR CARDIAC DISEASE

(75) Inventors: Hyo Joon Kim, 3-1001, Sunkyung APT, Sungpo-dong, Ansan 425-040 (KR); Key Seung Cho, Seoul (KR); Sang Min Lee, Seoul (KR)

(73) Assignee: Hyo Joon Kim, Ansan (KR)

( * ) Notice: Subject to any disclaimer, the term of this patent is extended or adjusted under 35 U.S.C. 154(b) by 110 days.

(21) Appl. No.: 11/581,146

(22) Filed: Oct. 16, 2006

(65) Prior Publication Data

US 2007/0122846 A1    May 31, 2007

Related U.S. Application Data

(62) Division of application No. 09/958,303, filed as application No. PCT/KR00/00882 on Aug. 10, 2000, now abandoned.

(30) Foreign Application Priority Data

Feb. 8, 2000    (KR) .................................. 2000-5808

(51) Int. Cl.
*G01N 33/53* (2006.01)
(52) U.S. Cl. .................. 435/7.1; 435/7.2; 435/7.91; 435/41; 435/69.6
(58) Field of Classification Search ................. 435/7.1, 435/7.2, 7.91, 41, 69.6
See application file for complete search history.

(56) References Cited

U.S. PATENT DOCUMENTS

| | | | |
|---|---|---|---|
| 5,856,160 A | 1/1999 | Hillman et al. | |
| 6,001,624 A | 12/1999 | Hillman et al. | |
| 6,558,903 B1 | 5/2003 | Hodge | |
| 6,777,182 B2 | 8/2004 | Baban et al. | |

OTHER PUBLICATIONS

Noma J. Med. Invest. 2005 vol. 52, p. 127-136.*
Nassaki et al. J. Biochemistry 1998 vol. 123, p. 128-135.*
The Journal of American Medical Assn., Eisenbrey et al., "Cardiac Troponin T and Point-of-Care Testing for Myocardial Infarction", vol. 274, No. 1, pp. 1343-1344 (Nov. 1995).
The Journal of Biological Chemistry, Matsuura, et al., "Human Adenylate Kinase Deficiency Associated with Hemolytic Anemia", vol. 264, No. 17, pp. 10148-10155 (1989).
Biochemistry, Kuby et al., "Rabbit Muscle Myokinase Sequence", vol. 23, No. 11, pp. 2392-2399 (1984).
J. Mol. Biol., W. Sachsenheimer et al., "Two Conformations of Crysalline Adenylate Kinase", vol. 114, pp. 23-36 (1977).
J. Mol. Biol., U. Enger et al., Structure of Adenylate Kinase-Inhibitor Complex, vol. 115, pp. 649-658 (1987).
Biochemistry and Molecular Biology Intl., Y. Lee et al., "Cloning and Characterization of cDNA for Human Adenylate Kinase 2A", vol. 39, No. 4, pp. 833-842 (Jul. 1996).
Genomics, G. Xu et al., "Characterization of Human AK3 cDNA and an AK3 Pseudogene", vol. 13, pp. 537-542 (1992).
The Journal of Biological Chemistry, M. Chiga et al., "Nucleotide Transphosphorylases from Liver", vol. 236, No. 6, pp. 1800-1805 (1961).
Biochemistry, G. J. Albrecht, "Nucleoside Triphosphate-AMP Transphosphorylase", vol. 9, No. 12, pp. 2462-2470 (1970).
European Journal of Immunology, G. Kohler and C. Milstein, "Derivation of established lines producing predefined antibody", 6:511-519 (1976).
Molecular Brain Research 62, T. Yoneda et al., "Identification of a Novel Adenylate Kinase System in the brain: Cloning of the fourth adenylate kinase", pp. 187-195 (1998).

* cited by examiner

*Primary Examiner*—Mark L Shibuya
*Assistant Examiner*—Jacob Cheu
(74) *Attorney, Agent, or Firm*—Stephen A. Bent; Foley & Lardner LLP

(57) ABSTRACT

The present invention relates to an immunological formulation and a diagnostic kit for cardiac disease using human mitochondrial adenylate kinase isozymes. The present invention provides an immunological formulation and a diagnostic kit for cardiac disease, which are featured by using mitochondrial adenylate kinase isozymes which exist in a myocardiac cell among muscle cells, but not in a skeletal muscular cell, as a diagnostic marker for cardiac disease and which enable more correct and easy diagnosis of cardiac disease.

2 Claims, 17 Drawing Sheets

M: φX174/Hae III Marker
1 : PCR Product

M1 : λ DNA *EcoR* I / Hind III Marker
 1 : Undigested
 2 : *EcoR* I Double Digested
 3 : Isolated and Purified Fragment
M2 : φX174 / *Hae* III M1 : λ DNA *EcoR* I + Hind III Marker
 1 : pQE30-AK3
 2 : pQE30-AK3 / *Bam* H I & *EcoR* I
M2 : φX174 / *Hae* III Western Blot Analysis M: Marker
1: Crude Extract
2: Ni-NTA Affinitive Chromatography
3: Gel-Filtration Elution SDS-Page M: Marker
1: Crude Extract
2: Ni-NTA Affinitive Chromatography
3: Gel-Filtration Elution A: SODIUM PHOSPHATE BUFFER(pH7.5) CONTAINING 1M KCl B: 0.1M GLYCIN HCl (pH 2.5)

SDS-Page

M : Marker
1 : Purified Recombinant AK1
2 : Purified Recombinant AK2
3 : Purified Recombinant AK3

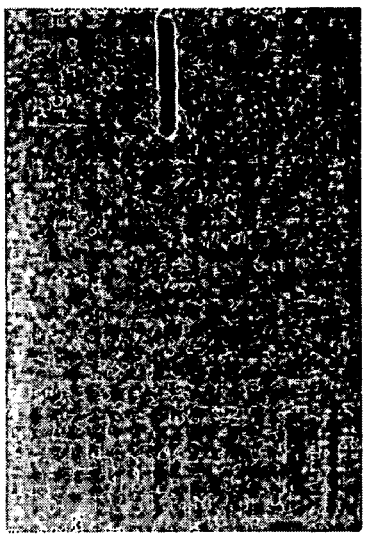

FIG. 12A
Western Blot Analysis
Anti-AK1 Antibody

M : Marker
1 : Purified Recombinant AK1
2 : Purified Recombinant AK2
3 : Purified Recombinant AK3

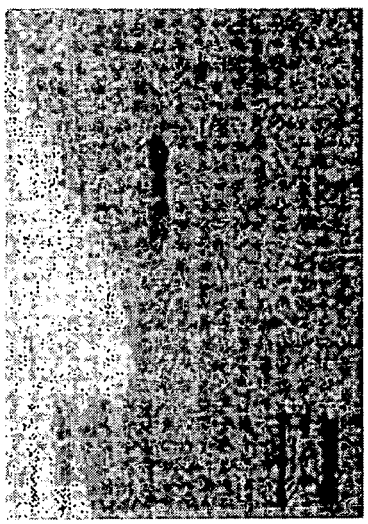

FIG. 12B
Western Blot Analysis
Anti-AK2 Antibody

M : Marker
1 : Purified Recombinant AK1
2 : Purified Recombinant AK2
3 : Purified Recombinant AK3

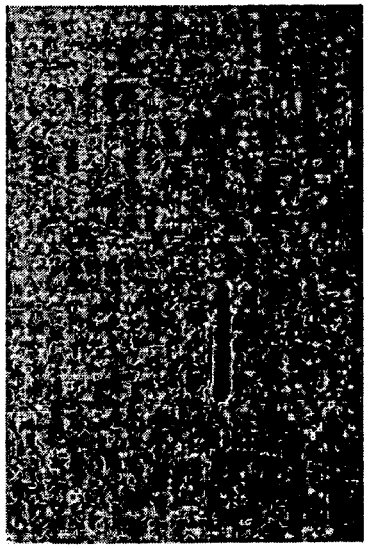

FIG. 12C
Western Blot Analysis
Anti-AK3 Antibody

M : Marker
1 : Purified Recombinant AK1
2 : Purified Recombinant AK2
3 : Purified Recombinant AK3

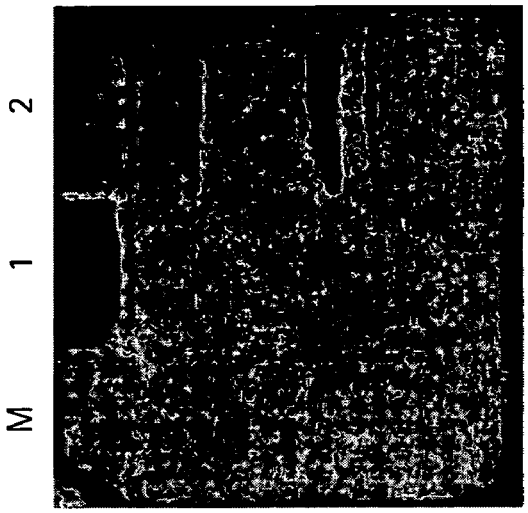
FIG. 13A Anti-AK1 Antibody
M: Marker
1: Skeletal Muscle
2: Cardiac Muscle
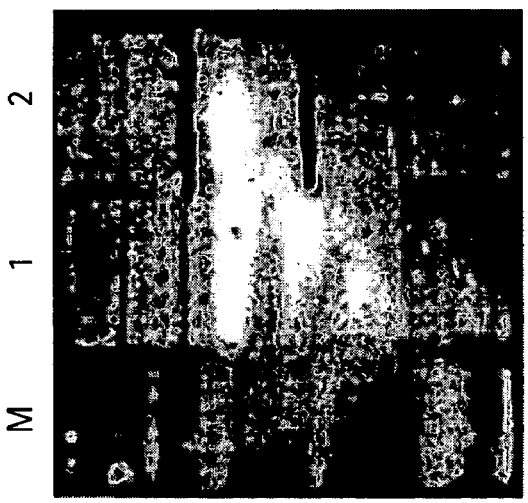
FIG. 13B Anti-AK2 Antibody
M: Marker
1: Skeletal Muscle
2: Cardiac Muscle
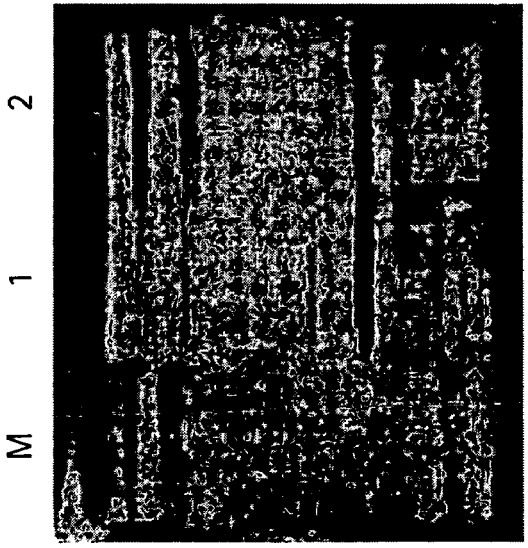
FIG. 13C Anti-AK3 Antibody
M: Marker
1: Skeletal Muscle
2: Cardiac Muscle

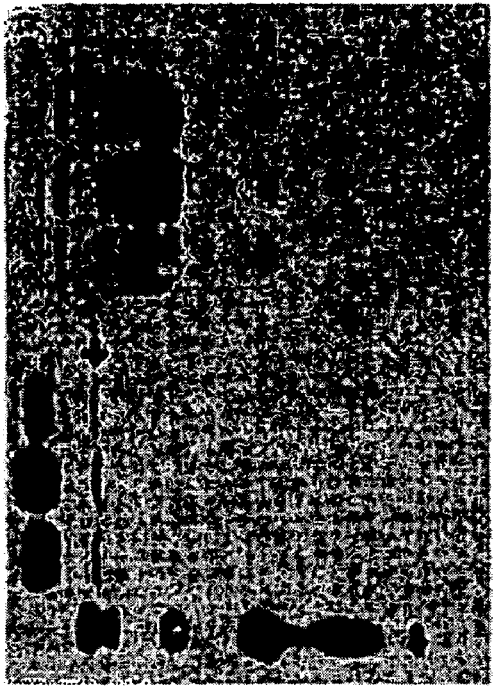

FIG. 14A

Western Blot Analysis
Anti-AK2 Antibody

Non-Substitution Condition
Substitution Condition

M  1  2  3     1  2  3

M : ECL Marker
1 : Myocardial Infarction Patient's serum
2 : Myocardial Infarction Patient's serum
3 : Myocardial Infarction Patient's serum

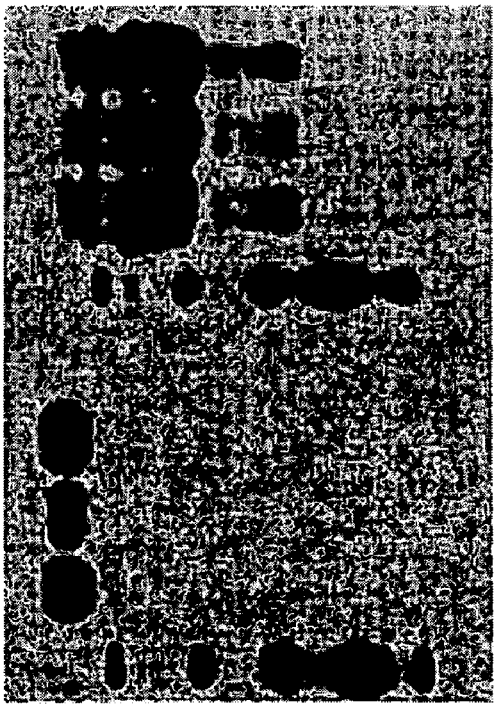

FIG. 14B

Western Blot Analysis
Anti-AK3 Antibody

Non-Substitution Condition
Substitution Condition

M  1  2  3     1  2  3

M : ECL Marker
1 : Myocardial Infarction Patient's serum
2 : Myocardial Infarction Patient's serum
3 : Myocardial Infarction Patient's serum SDS-Page 1 : Acute Myocardial Infarction Patient's Serum
2 : Acute Myocardial Infarction Patient's Serum
3 : Acute Myocardial Infarction Patient's Serum
4 : Leg Bone-fractured Patient's Serum
5 : Healthy Person's Serum
6 : Purified AK1
7 : Purified AK1
8 : Purified AK1

ANTI-HUMAN MITOCHONDRIAL ADENYLATE KINASE ISOZYME ANTIBODY, DIAGNOSTIC FORMULATION AND DIAGNOSTIC KIT FOR CARDIAC DISEASE

CROSS-REFERENCE TO RELATED PATENT APPLICATIONS

This application is a divisional application of U.S. application Ser. No. 09/958,303 filed Feb. 19, 2002; now abandoned which is the U.S. National Phase of PCT/KR00/00882 filed Aug. 10, 2000; which claims priority from Korean Application No. 2000/5808 filed Feb. 8, 2000, the contents of which are relied upon and incorporated by reference.

BACKGROUND OF THE INVENTION

Technical Field

The present invention relates to an immunological formulation and a diagnostic kit for cardiac diseases using human mitochondrial adenylate kinase isozymes, more particularly to an immunological formulation and a diagnostic kit for cardiac disease characterized by using an adenylate kinase isozyme AK3 having a cardiac muscle-specific expression as a diagnostic indicator of cardiac disease such as a myocardial infarction, angina pectoris and thus enabling more correct and easy diagnosis of cardiac disease without misdiagnosis due to excellent diagnostic discrimination.

Cardiac diseases such as acute myocardial infarction as one of the adult diseases predominantly occur to 40's latter half-people, and the patients who died of the cardiac diseases are gradually increasing in the world. Average 200 or more tests per month of diagnosis for the cardiac disease are commenced in a domestic general hospital. Every year a few million people suffering from chest pain attend the emergency room of the hospital in the United States of America.

A general method for diagnosing a cardiac disease in the past from a person who is suffering from a chest pain is to use an electrocardiogram ("ECG" or cardiac sonographs). When diagnosing a myocardial infarction by using ECG, the myocardial infarction has been determined by the changes of an abnormal ST-T wave and a Q wave of ECG. However, 50% or more of myocardial infarction patients who attended the hospital were misdiagnosed, about 5% of the said patients returned to their homes, and 16% of the said patients were misdiagnosed to death.

In order to solve these problems, the biological markers for a myocardial infarction have been developed. The ideal biological markers for myocardial infarction preferred to have the following requirements.

First, it should exist in only cardiac muscle cells and be released into the blood with the necrosis of the myocytes.

Second, it should be rapidly released into the blood after the cardiac muscle is hurt, as this depends on the cellular distribution and the molecular size of the biological marker.

Third, the relation between the extent of the cardiac injury and the released amount of the biological marker should be linear.

Fourth, a special training and techniques for assay should not be required, and the cost of the reagents required for the detection should be continuously cheap.

Fifth, pathologic concentration of the biochemical marker in blood should be increased after the patients feel the pain in their chests.

Sixth, the released biological markers should be rapidly removed so as to confirm the continuous myocardial infarction. However, unfortunately, the biological markers satisfying all of these requirements are not still present.

At present, a creatine kinase(CK) mass assay and troponin test are employed for diagnosing myocardial infarction as biochemical markers. Since CK has MM type in muscle tissue, BB type in brain and myelon, and hybrid MB type in skeletal muscle or cardiac muscle, serum concentrations of them are used as an indicator of tissue injury of the heart. Specifically, CK-MB is known as an enzyme indicating the extent of the acute myocardial infarction, and it shows about a 5% change range of blood potency in all the muscular diseases such as burn, trauma, cardiac and skeletal muscle disease.

However, the diagnosis for myocardial infarction employing CK-MB had a limited detection problem, and about 20% of a false signal which reduces the detection accuracy, it could not be a reliable diagnosis. At present, the diagnostic standards for myocardial infarction stipulated by World Health Organization(WHO) are as follows: (1) a traditional chest pain, (2) an abnormal Q wave of ECG, and (3) biochemical markers should be over the reference range. If at least two standards among them are applicable to a person, it is definitely diagnosed as a myocardial infarction patient. Biochemical markers should be included as part of the triad of for AMI diagnosis.

Alternatively, Boyce N. et al. developed a cardiac troponin T(cTnT) test to reduce a misdiagnosis by using creatine kinase (CK-MB) as a conventional cardiac injury marker [refer to "*Clinical Laboratory News*, 22(1), 1-14(1996)"]. This test was officially recognized by the United States Food and Drug Administration (FDA), and commercialized as a product by Boehringer Manheim Diagnostics Co., Ltd. in Germany. And the United States has used the product since November 1996, but now use Troponin I test since it was confirmed that it is cross-reacted with skeletal muscle-derived troponin T. However, cTnT and cTnI are released within 12-24 h after chest pain thus cannot be used as early markers [refer to "Eisenbrey et al., (1995) The Journal of American Medical Association, 74, 1343-1344)"], Therefore, these tests could not be satisfactorily alternative tests. Accordingly, they are employed only as aid-means of CK-MB test. The said diagnostic methods are limitly employed only in few general hospitals, since they require expensive assay equipments, a heart specialist and a highly trained manpower, and thus increase an expensive diagnosis cost. Further, the patients requiring a continuous detection hardly use the troponin, because a medical insurance to the troponin is allowed only once in Korea.

As mentioned above, the conventional biological marker for diagnosing cardiac diseases cannot be satisfied in view of a diagnosis accuracy and diagnostic time after onset of AMI. Accordingly, it has been demanded that a new diagnostic indicator for a cardiac muscle injury which enables more accurate and rapid diagnosis without expensive assay equipments, and small clinic and a person to diagnose a cardiac diseases.

SUMMARY OF THE INVENTION

The object of the present invention provides an immunological formulation and a diagnostic kit for cardiac disease and myocardial infarction using human mitochondrial adenylate kinase isozymes which enable an excellent accuracy and sensitivity, characterized by that the diagnostic indicator candidate material satisfying all the ideal diagnostic indicators requirements for myocardial infarction specifically exist in a heart muscle tissue, and that anti-AK antibodies specifically recognizing human mitochondria adenylate kinase isozyme having different subcellular distribution are used.

That is to say, the present invention provides an immunoglobulin specific to human mitochondria adenylate kinase isozymes(AK) and a portion thereof, characterized by that the immunoglobulin is produced in an animal species reactive to the immunogen including a human mitochondria adenylate kinase isozyme(AK) and a portion thereof.

The present invention also provides an immunological formulation consisting of a combination of an immunoglobulin and a detection marker.

The present invention also provides a diagnostic kit for cardiac diseases comprising an immunoglobuline according to the present invention binding a detection marker and a pharmaceutically acceptable carrier.

The present invention also provides a method for detecting a human mitochondrial adenylate kinase isozyme 3(AK3) in a detection sample, comprising the following steps (a), (b) and (c):
 (a) producing an immune complex by reacting a detection sample and a control sample with anti-adenylate kinase isozyme 3(AK3) antibody or a portion thereof, respectively;
 (b) detecting the immune complex obtained in the said step(a); and
 (c) comparing the detected results of detection sample and control sample.

BRIEF DESCRIPTION OF THE DRAWINGS

The above object, other features and advantages of the present invention will become more apparent by describing the preferred embodiment thereof with reference to the accompanying drawings, in which:

FIG. 12 is-a drawing illustrating the result of a cross-reactivity assay among the purified anti-AK isozyme antibodies;

FIG. 13 is a drawing illustrating a tissue distribution of AK isozymes;

FIG. 14 is a drawing illustrating the results of Western blot analysis obtained by using an anti-AK2 antibody and an anti-AK3 antibody of the myocardial infarction patients' serum under the condition of substitution or non-substitution;

DETAILED DESCRIPTION OF THE PREFERRED EMBODIMENTS

The preferred embodiments of the present invention will be described in detail with reference to the annexed drawings.

The term "biological sample" herein means a body fluid or a portion thereof, for example urine, blood, serum and blood plasma separated from human body.

The term "detection marker" herein means a marker for detecting an immune complex, for example radioactive isotope indicator, gold particle, enzyme, chemoluminescent compound, fluorescein, phycobiliprotein, rare earth chelate, fluorescent material such as rodamine, enzyme cofactor, biotin, streptavidin, and the like.

The term "monoclonal" herein means an immunoglobulin cell derived from a single cloned hybridoma cell system and a system which enable to produce a single type of antibody, which are produced by cell fusion such as hybridoma cell line.

The term "polyclonal" herein means a system which enable to produce immunoglobulins derived from many kinds of cells having a general polyaffinity to an immunogen, wherein an "immunoglobulin" generally means one synthesized in the organism of animal having an acquired immunity.

The term "mitochondria adenylate kinase isozyme" herein means a mitochondria adenylate kinase isozyme per se such as mitochondria adenylate kinase isozyme 2(AK2) and mitochondria adenylate kinase isozyme 3(AK3), their gene recombinants protein and artificial mutant and natural mutant.

The term "a portion of mitochondria adenylate kinase isozyme" herein means a digested or truncated peptide fragment of mitochondria adenylate kinase isozyme including an antibody-reactive portion of mitochondria adenylate kinase isozyme.

The adenylate kinase(AK) is an enzyme maintaining a rapid dynamic equilibrium between adenine nucleotides by catalyzing a reversible phosphoric acid transfer reaction of XTP, ADP and AMP in a cell as shown in the below reaction:

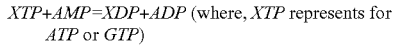

$XTP+AMP=XDP+ADP$ (where, $XTP$ represents for $ATP$ or $GTP$)

The said enzyme is one of the enzymes required for phosphorylation reaction relating to a cell metabolism activity and a signal transfer. It is also known to participate in energy metabolism, apoptosis, tumorigenesis and the like, and is reported to include about 40 kinds of the isozymes in a biological system [refer to "Matsuura, S., Igarashi, M., Tanizawa, Y., Yamada, M., Kishi, F., Kajii, T., Fujii, H., Miwa, S., Sakurai, M., & Nakazawa, A. (1989) J. Biol. Chem, 264, 10148-10152"].

Figure 1:
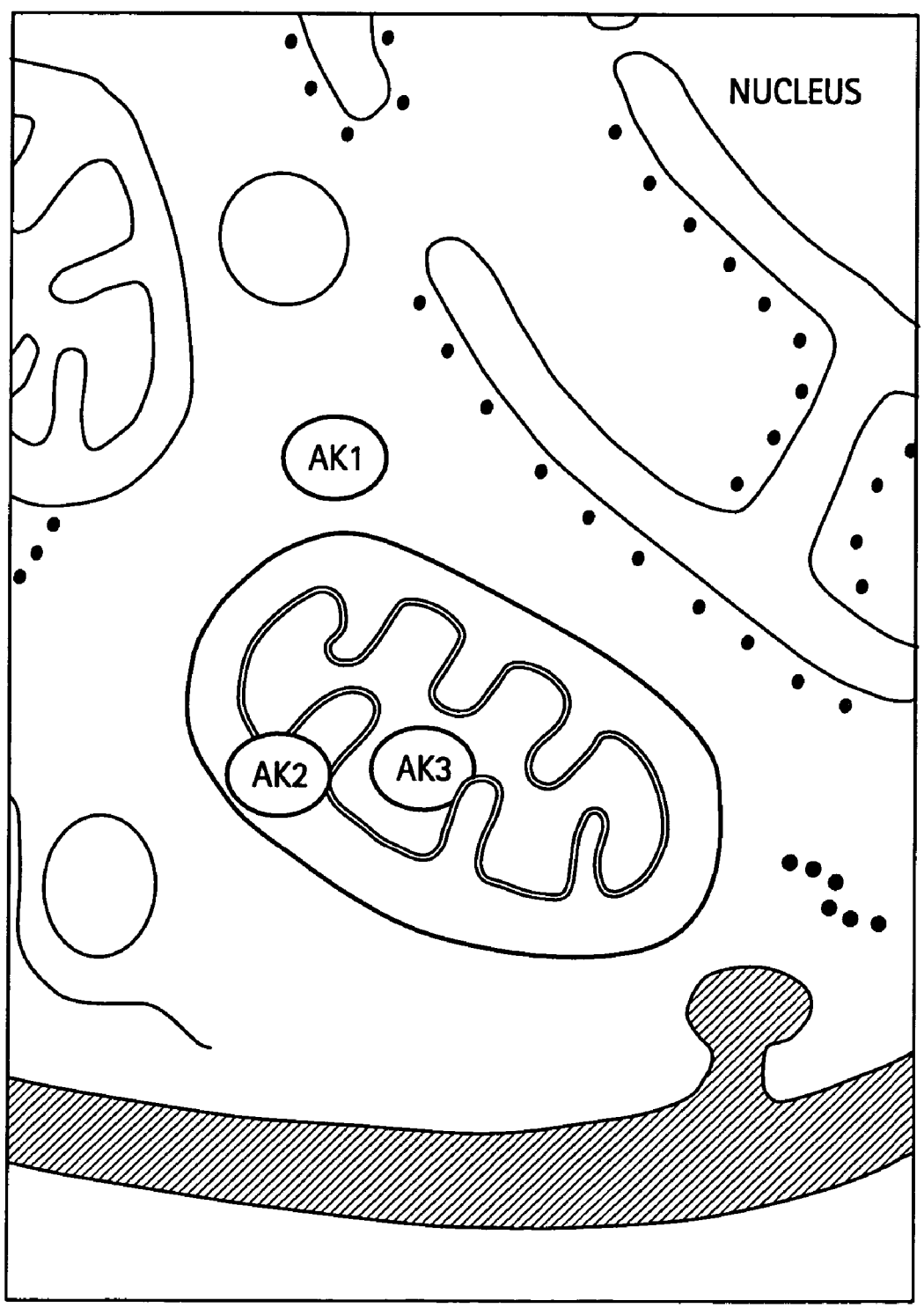
FIG. 1 is a schematic drawing illustrating a subcellular distribution of adenylate kinase isozymes in cell.

As shown in FIG. 1, a cell of vertebrata has 3 subtypes of isozyme, i.e. AK1 (EC 2.7.4.3) in a cytoplasm, AK2 in a mitochondria intermembrane space, and AK3 (EC 2.7.4.10) in a mitochondria matrix [refer to "Kuby, S. A., Palmieri, R. H., frischat, A., Wu, L. H., Maland, L., & Manship, M. (1984) Biochemistry 23, 2392-2399; Sachsenheimer, W., & Schulz, G. E. (1997) J. Mol. Biol. 114, 23-36; Egner, U., Tomasselli, A. G., & Schulz, G. E. (1978) J. Mol. Biol. 195, 649-658"]. A putative human AK3 has been identified based on its similarity to bovine and murine AK3. However, the human AK3 cDNA is more closely related to the newly identified murine AK4 genes, and the human AK3 gene has, therefore, been renamed AK4 (Yoneda, T., Sato, M., Maeda, M., Takagi, H. (1998) Identification of a novel adenylate kinase system in brain; cloning of the fourth adenylate kinase. Mol. Brain. Res., 62, 187-195].

In this document, we will use the name AK3 instead of AK4 because murine AK4 is a brain type isozyme but AK3 is not expressed in human brain. In human, AK5 was recently identified as brain-type isozyme.

Two subtype genes of AK2A and AK2B in a human gene-AK2(hAK2) have been cloned. Further, mRNA of hAK1 and hAK2 has been confirmed in many kinds of tissues such as a cardiac muscle, skeletal muscle, liver and the like [refer to "Lee, Y., J. W. Kim, 1, A. Lee, H. B. Kang, Y. K. Choe, H. G. Lee, J. S. Lim, H. J. Kim, C. K. Park, and I. S. Choe, (1996) Biochem. Mol. Biol. International, 39(4), 833-842"]. These genetic products have a tissue-specific expression aspect. It is reported that AK1 is expressed in both cardiac muscle and skeletal muscle, but AK2 is not expressed in a skeletal muscle [refer to "Lee, Y., J. W. Kim, S. M. Lee, H. J. Kim, K. S. Lee, C. Park, & L. S. Choe (1998) J. Biochem.-Tokyo, 123, 47-54"].

Human adenylate kinase isozyme 3(AK3) is a phosphoric acid transfer enzyme consisting of 223 amino acids, and is also called "nucleosidetriphosphate-adenylate phosphotransferase." Array of human gene AK3 and primary array of amino acid were confirmed by Xu et al. [refer to "Xu, G., O'Connell, P., Stevens, J. and White, R. (1992) Characterization of human adenylate kinase 3(AK3) cDNA and mapping of the AK3 pseudogene to an intron of the NF1 gene. Genomics 13; 537-542"]. A sequence of human AK3 amino acid is shown in a sequence No. 1 of a sequence list attached herewith.

Human adenylate kinase isozyme 3 catalyzes the below reaction 2:

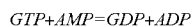

GTP+AMP=GDP+ADP

[refer to "Chiga, M., Rogers, A. E., Paut, G. W. E. (1961) J. Biol. Chem., 236, 1800; Albrecht, G. J., (1970) biochemistry, (9:2426)"].

Research on AK3 enzyme has not been vigorously commenced in comparison to the other enzymes, and a tissue specificity of AK3 enzyme in human body has not been reported yet.

It has been found that the genetic defect of AK enzyme in human body cause a hereditary hemolytic anemia [refer to "Matsuura, S., Igarashi, M., Tanizawa, Y., Yamada, M., Kishi, F., Kajii, T., Fujii, H., Miwa, S., Sakurai, M. and Nakazawa, A. (1989) J. biol. Chem. 264, 10148-10152)"] and that thiamine pyrophosphate is bio-synthesized by the cooperation of creatine kinase and AK in a muscle and brain tissue.

For the first time, the present inventors have found that AK3 is also expressed in a cardiac muscle same as AK2, but is not expressed in a skeletal muscle, and they applied these facts to a diagnosis for a cardiac disease such as myocardial infarction.

The present inventors cloned the mitochondria isozymes, the genes of AK2 (hAK2) and AK3 (hAK3) from human muscular tissue to construct pQE-AK2 and pQE-AK3 expression vectors, and then isolated and purified genetic recombinant AK2 and AK3 in a large amount by incubation of transformed coliform bacilli to attain a genetic recombinant E. Coli expression system of 1.1 mg of AK2/L broth and 9.8 mg of AK3/L broth.

Recombinant hAK isozyme has been confirmed by amino acids composition analysis. It has been confirmed that a specific activity and pI value of hAK2 are 1,000 U/mg and 6.6, respectively, and that a specific activity and pL value of hAK3 are 400 mU/mg and >11.7, respectively. Such physicochemical properties are similar to those reported for AK3 isozyme isolated from a cattle liver.

In order to review a tissue-specific expression aspect so as to find physiological function of AK isozyme, polyclonal antiserum of rabbit was derived by using hAK1, hAK2 and hAK3, and anti-hAK1, anti-hAK2 and anti-AK3 antibodies was attained by removing the antibodies which cross-recognizing isozymes therebetween. At the result of immunohistochemistry for paraffin embedded tissues by using the said antibodies, hAK1 was detected all the tissues, but hAK2 was detected only in liver, brain, cardiac muscle, kidney and lung, and hAK3 was detected only in liver, cardiac muscle, kidney and lung. Specifically, it was confirmed that AK1 was detected in both of two tissues even in Western blot analysis for brain, cardiac muscle and skeletal muscle, but AK2 and AK3 were not expressed in skeletal muscle and showed a cardiac-specific expression. Therefore, a different distribution pattern of adenylate kinase isozyme depending on human organs, especially between cardiac muscle and skeletal muscle proves that a possibility to be used as a clinical marker for a cardiac cell injury is very high.

The immunoglobulin according to the present invention is featured by being produced from animal system reactive with immunogen comprising human mitochondria adenylate kinase isozyme (AK) and a portion thereof. The said human mitochondria adenylate kinase isozymes are preferably human mitochondria adenylate kinase isozyme 2 (AK2) and human mitochondria adenylate kinase isozyme 3 (AK3). Such immunoglobulins (monoclonal or polyclonal) used in the present invention are limited to IgA, IgG, IgM, IgD, IgE or IgY, all the immunoglobulin can be used. It is not necessary to use a complete antibody, but a fragment of antibody including an antigen binding region, for example Fab, Fab' or F(ab)'2 fragments can be used.

Such adenylate kinase isozyme-specific immunoglobulins are obtained from an animal serum immunized with a purified adenylate kinase isozyme, from a hybridoma cell produced by a fusion of a splenic lymphocyte and myeloma cell, or from lymphocyte transformed in vitro. More specifically, adenylate kinase isozyme-specific monoclonal antibody can be produced by a well-known fusion method in this art [refer to "Kohler and Milstein (1976) European Journal of Immunology 6:511-519"]. The said monoclonal antibody was deposited to the deposit authority of Korean Cell Line Research Foundation (KCLRF) in the Cancer Research Center of the Medical College of Seoul National University (address: Youn-geon-dong, Chongro-ku, Seoul, Korea) as deposit No. KCLRF-BP-00030 on May 19, 2000. In the above-mentioned method, one group of two cell groups fused to produce "hybridoma" which secretes antibody is used as a cell of a immunologically suitable animal host such as a mouse injected with adenylate kinase isozyme, and the other cell group is fused as cancer or myeloma cell line. Such two cell groups are fused by a well-known method in this art using a polyethylene glycol and the like. And then, antibody-producing cells are proliferated by standard tissue incubation. The homogeneous cell group is obtained by subcloning in a limited dilution technique, and then a hybridoma that can produce an adenylate kinase isozyme-specific immunoglobulin, is incubated in vivo or in vitro by standard technique in a large amount.

Monoclonal antibody obtained in the above method may be used without purification, but can be used preferably after purification in a high purity by a conventional method. Such purification method includes, for example, salt precipitation, ion-exchange chromatography and affinity chromatography.

Polyclonal antibody used in the present invention can be produced by a conventional method wherein the purified adenylate kinase isozyme 2 or adenylate kinase isozyme 3 is injected to an animal, and then the serum including an antibody collected from the animal is obtained. The said polyclonal antibody can be purified by any one of the conventional methods in this art, and can be produced from animal host of any one of goat, rabbit, sheep, monkey, horse, pig, cow, dog and the like.

According to the present invention, the adenylate kinase isozymes can be used following isolation of it by a conventional method or biosynthesizing many kinds of its fragments by a conventional genetic engineering technique. Alternatively, the adenylate kinase isozyme 3 peptides can be chemically synthesized by an organo-protein synthesis method.

In another embodiment of the present invention, an immunological formulation binding an immunoglobulin of the present invention with detection marker is provided. For this immunological formulation, a detection marker can be selected a group consisting of radioactive indicator, gold particles, enzyme, chemoluminescent compound, fluorescent material, enzyme cofactor, streptavidin, biotin, and the like.

According to the present invention, an adenylate kinase isozyme-specific antibody is used for detecting an adenylate kinase isozyme in a biological sample including blood or other body fluid. Specifically, adenylate kinase isozyme (AK) in a biological sample can be confirmed by detecting the said bound immunoglobulin from contact of immunological formulation of the present invention with the biological sample. The detection method used in the present invention is not specifically limited, for example, there are two methods, one is a sandwich enzyme-linked immunosorbent assay (ELISA) wherein an antibody is attached to microtiter plate or 96-well plate to react a serum sample and the secondary antibody is attached thereto to enzymologically color-develop it, and the other is the assay wherein the protein isolated by electrophoresis on the polyacrylamide gel is blotted on nitrocellulose or PVDF membrane to react antibody.

According to the present invention, the kit for diagnosing cardiac disease comprises an immunoglobulin of the present invention and a pharmaceutically acceptable carrier. Since only protein component has to be replaced to make a diagnostic kit, the kit of the present invention can be produced in the patch or strip type. For example, the diagnosis kit for cardiac disease of the present invention may include the antibody specific to an adenylate kinase isozyme and an adenylate kinase isozyme contained in each test sample, respectively. An adenylate-kinase isozyme and an adenylate kinase isozyme-specific antibody may be fixed on the solid phase of the membranes and be labeled. When employing an enzyme label, the kit of the present invention may comprise enzyme substrate. In case of assay by using the second antibody labeling the immune complex, the kit of the present invention may comprise anti-adenylate kinase isozyme antibody or an adenylate kinase isozyme-specific second antibody. The kit of the present invention can additionally include a suitable standard, positive or negative control, and other statement for use.

In other embodiment of the present invention, there provides a method for detecting an adenylate kinase isozyme (AK) in a test sample, comprising the below steps:

(a) producing an immune complex by reacting a detection sample and a control sample with an anti-adenylate kinase isozyme(AK) antibody or a portion thereof, respectively;

(b) detecting the immune complex obtained in the said step (a); and (c) comparing the detected results of the detection sample with the detected result of the control sample.

In this method, the said detecting step can be commenced by immunofluorescence antibody method, enzyme-substrate color-development method, chemoluminescent compound binding method, or gold particle complex method. For the said control sample, the serum which was detected to be positive by immunofluorescence antibody method, enzyme-substrate color-development method, chemoluminescent compound binding method, gold particle complex method can be used. However, the detection method to be used in the present invention is not limited to the said method, but any one of the conventional detection methods may be used.

Now, the preferred embodiments of the present invention will be described in detail by the following Examples without limiting the scope of the invention in any way.

EXAMPLE 1

Cloning of AK3 Gene (Total RNA Extraction From Human Skeletal Muscle)

In order to isolate RNA, 1 ml of RNAzol (4 M guanidine thiocyanate, 25 mM sodium citrate, 0.5% salcosyl, 0.1 M 2-mercapto ethanol) was added to 100 mg of a muscular tissue, and then homogenized, and 100 µl of chloroform was added thereto, shaken for 15 seconds and left in ice for 15 minutes. The cell lysate solution was centrifuged in 12,000×g for 15 minutes to remove the insoluble cell debris. The supernatant was transferred to a fresh tube, and an equal amount of isopropanol was added thereto and mixed each other to give a mixture which was incubated at the temperature of −70° C. for 15 minutes. And then, the mixture was centrifuged at the temperature of 4° C., 12,000×g for 15 minutes to precipitate RNA pellets. The RNA pellets was washed with 75% ethanol and dried, and then 100 µl of DEPC-treating water was added thereto to extract a total RNA.

(Preparation of AK3 cDNA by RT-PCR)

The above-isolated 10.5 µl of total RNA was mixed with 1 µl of 500 ng/µl oligo dT, 1.5 µl of 2.5 mM dNTPs, 1 µl of 100 mM DTT, 1 µl of 200 unit/µl MMLV reverse transcriptase, 6 µl of 5× reverse transcriptase buffer and 9 µl of DEPC-treating water to make 30 µl of total volume, was reacted at the temperature of 42° C. for 30 minutes, and then was inactivated at the temperature of 75° C. for 30 minutes. For composition of PCR reaction mixture, the above-synthesized cDNA was used as a template cDNA. Eight µl of 2.5 mM dNTPs, 1 µl of 5 unit/µl Ex taqDNA polymerase, 10 µl of 10× DNA polymerase buffer, 1 µl of sense-primer (SEQ ID NO: 1) and 1 µl of antisense-primer (100 pmol/µl) (SEQ ID NO: 2) were added thereto, and the distilled water was added thereto to make 100 µl of total volume. The mixture was denatured at the temperature of 98° C. for 10 seconds, annealed at the temperature of 55° C. for 30 seconds, extended at the temperature of 72° C. for 40 seconds, and this polymerase chain reaction was repeated for 35 cycles. In this procedure, two primers, i.e. 5'-GGATCCATGGCTTCCAAACTCCTGC-3'

Figure 2:
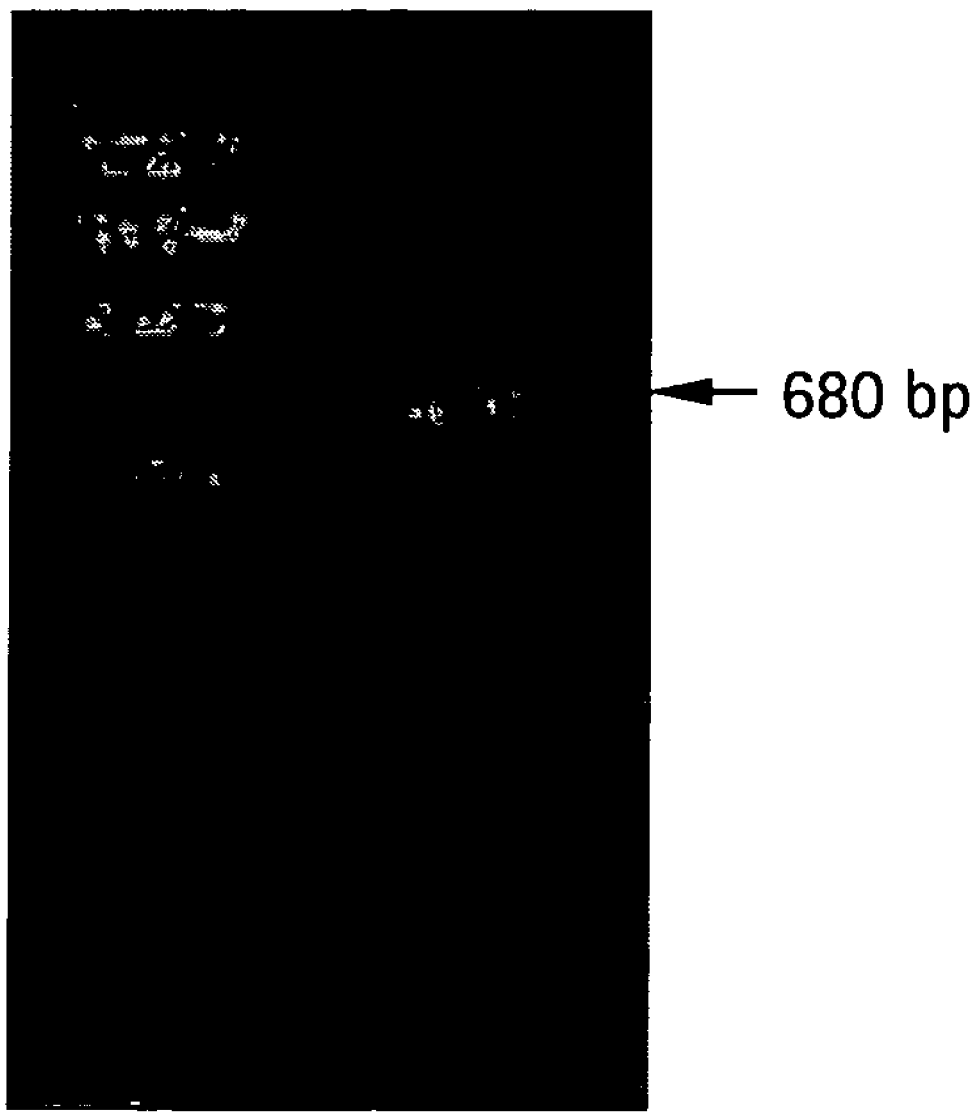
FIG. 2 is a drawing illustrating an electophoresis for the PCR product of an adenylate kinase isozyme 3(AK3)

(sense) and 5'-CAGGGTCAATATGCTTCTTTGG-3' (antisense) were used, and PCR product was detected in 1% agarose gel (refer to FIG. 2).

[Construction of AK3 Subcloning Vector (pCR2.1-AK3)]

Figure 3:
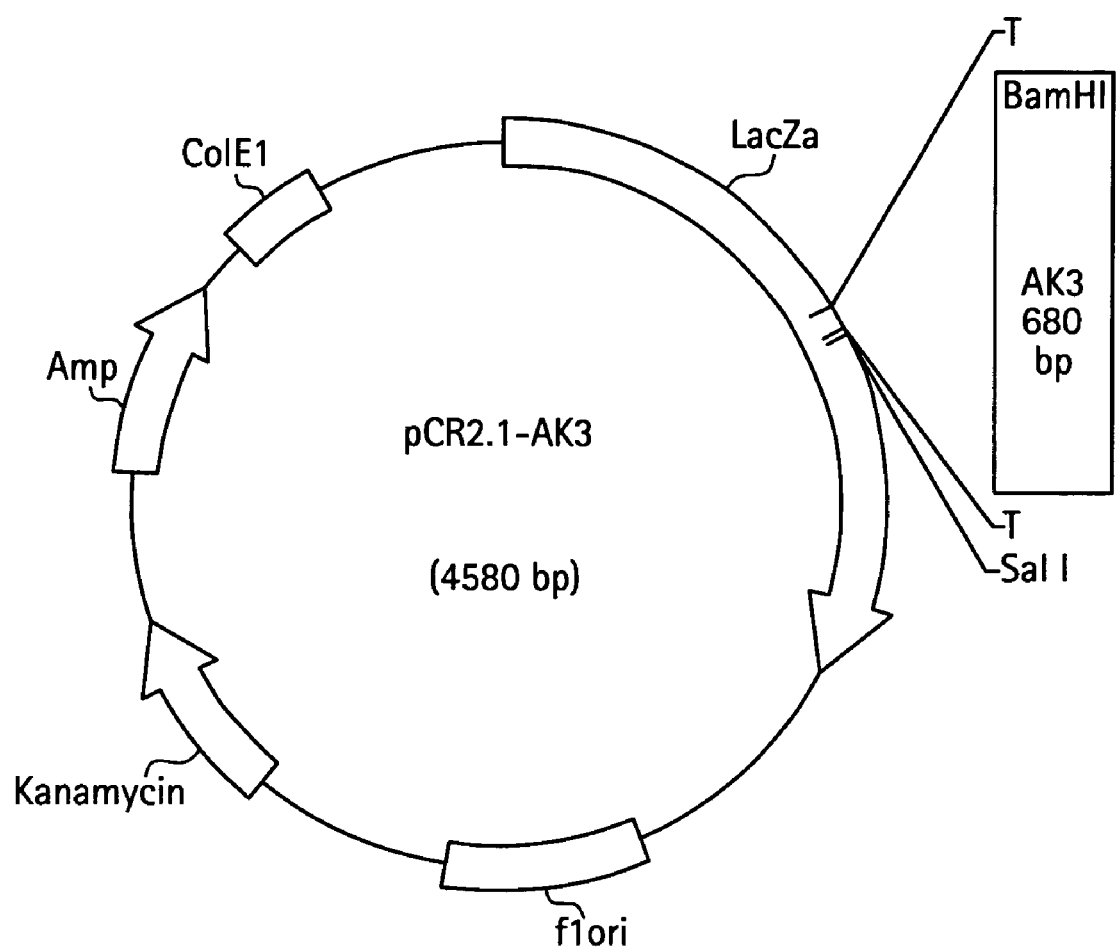
FIG. 3 is a gene map of PCR2.1-AK3.
Figure 4:
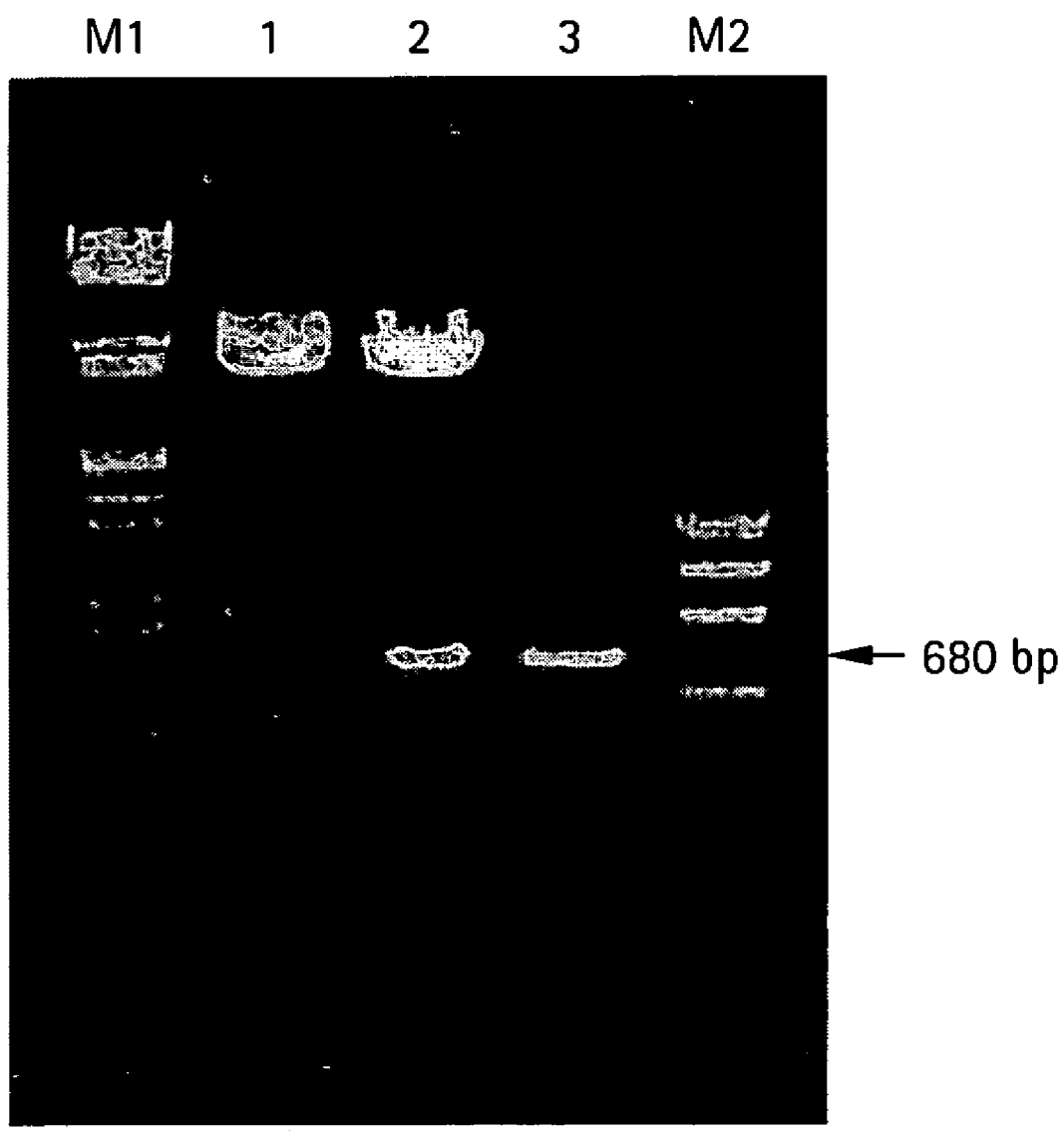
FIG. 4 is a drawing illustrating a plasmid mapping by specific restriction enzyme digestion.

AK3 PCR product having 680 bp was purified from agarose gel by using a gel-extracting kit, and cloned by using pCR2.1 (invitrogen) PCR cloning kit (refer to FIG. 3). For the ligation mixture, 1 µl 50 ng of linearized pCR2.1 vector, 5 µl of PCR product, 1 µl of 4 unit/µl T4 DNA ligase, 1 µl of 10× ligase buffer and 2 µl of $dH_2O$ were mixed to be total volume of 10 µl, and then reacted at the temperature of 16° C. for 12 hours. *E. coli* strain JM 109 as a host cell was used to transform the constructed pCR2.1-AK3 plasmid. Two 1 µl of ligation mixture was added to 50 µl of JM 109 competent cell, left in ice for 30 minutes, was heat-shocked at the temperature of 42° C. for 45 seconds, and dipped in ice for 2 minutes. Two hundred and fifty µl of SOC culture medium was added thereto, incubated at the temperature of 37° C. and the rotating speed of 225 rpm for 1 hour. Hundred µl of the cultivated medium was plated on LB/ampicillin plate comprising X-gal and IPTG, and incubated at the temperature of 37° C. overnight. 10 colonies among the produced white colonies were selected, added to the LB culture medium containing 50 µg/ml of ampicillin, respectively and then incubated at the temperature of 37° C. overnight. For the incubation product, plasmid DNA was isolated by using a plasmid prep kit. Five µl of the isolated plasmid DNA was mixed with 1 µl of EcoR1, 1 µl of EcoR1 reaction buffer and 3 µl of $dH_2O$, reacted for 1 hour and was subjected to an electrophoresis in 1% agarose gel. It was confirmed that PCR product was subcloned (refer to FIG. 4). Base sequence for the PCR product-inserted plasmid was confirmed by using an automatic DNA sequencer in order to know correct subcloning. At this time, as primers, M13 reverse primer (sense primer) and T7 promoter primer (anti-sense primer) were used.

EXAMPLE 2

Construction Of AK3 Expression Vector and Isolation and Purification of Recombinant AK3

Figure 5:
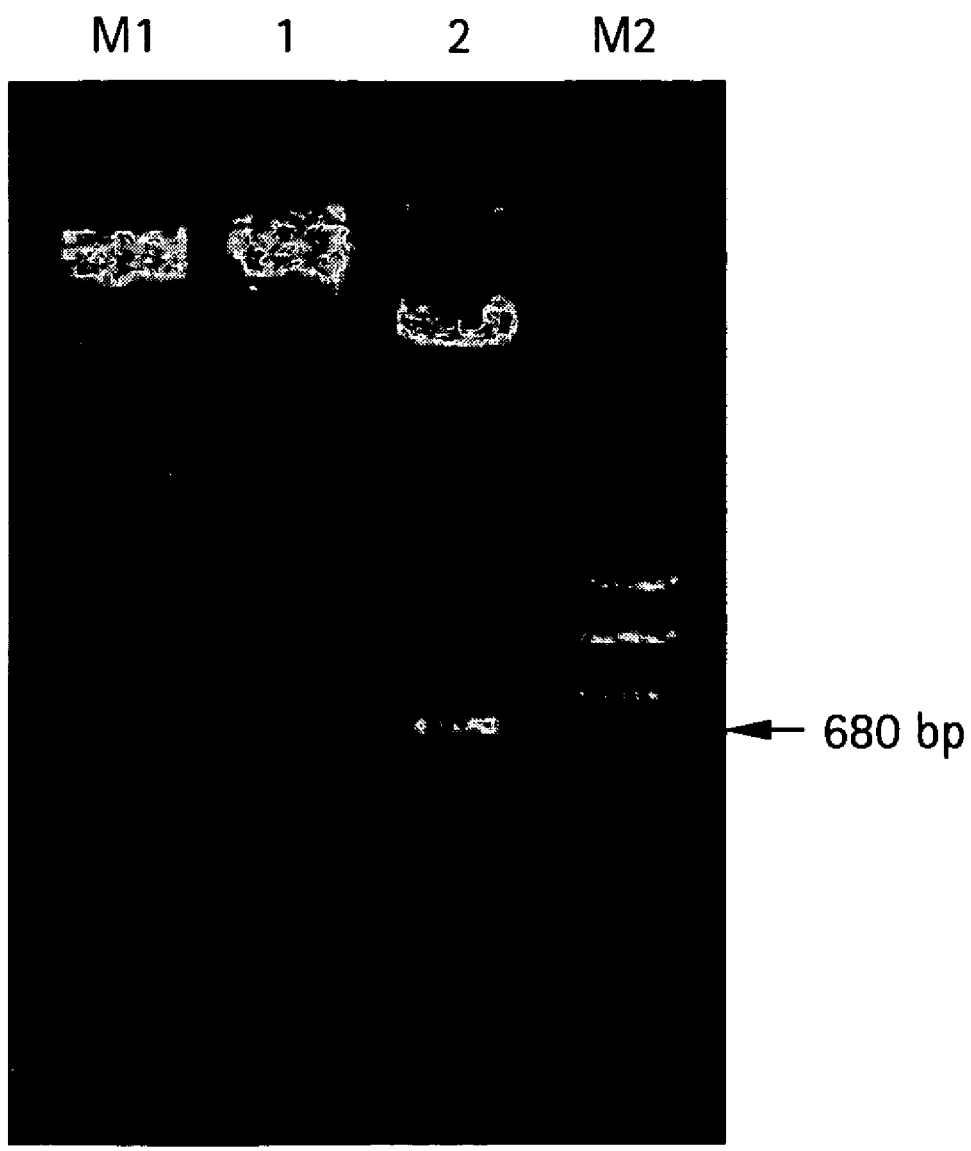
FIG. 5 is a drawing illustrating a restriction enzyme digestion pattern.
Figure 6:
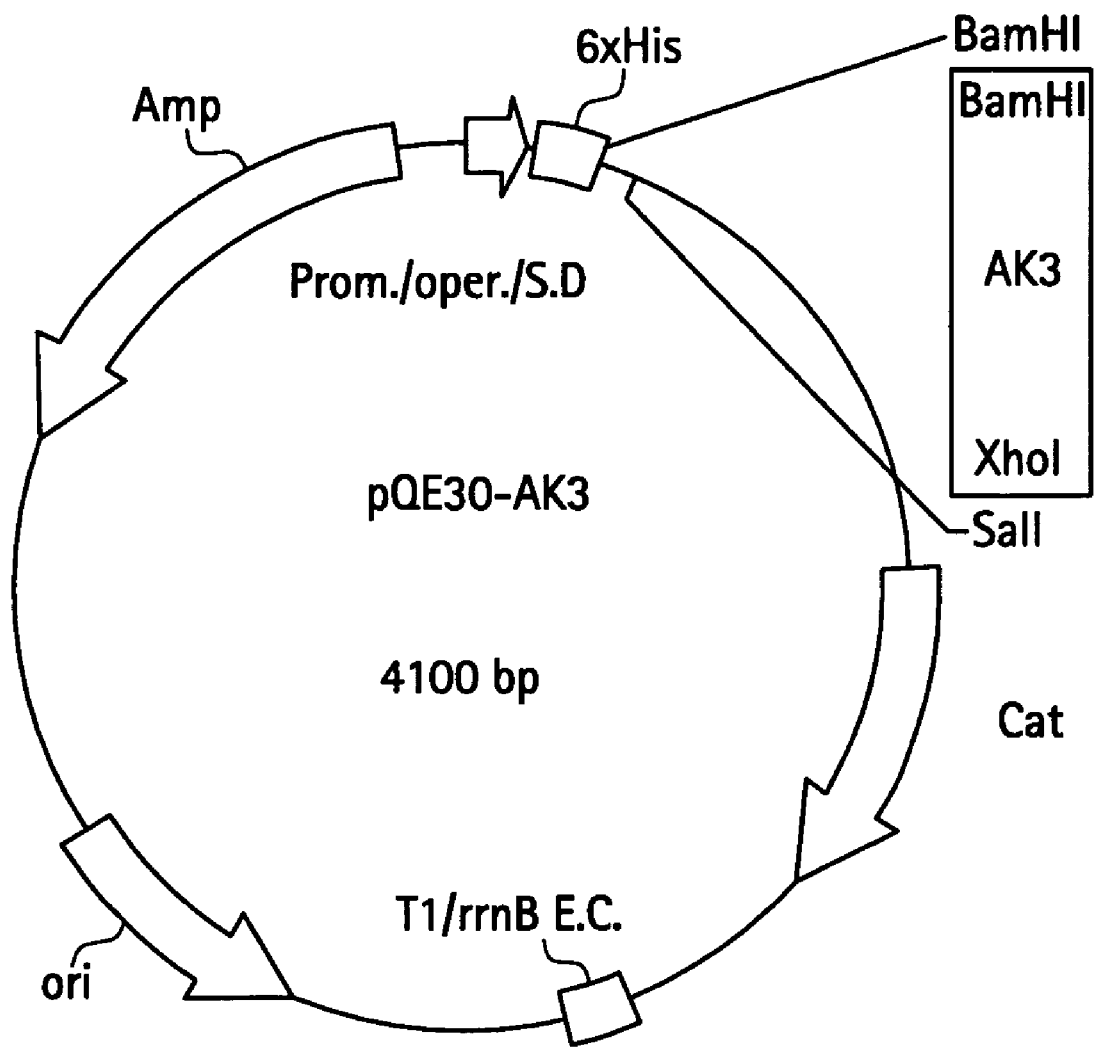
FIG. 6 is a gene map of pQE 30-AK3.

After pCR2.1-AK3 vector subcloning AK3 gene was double-digested by BamHI and Xho1, an insert was eluted from agarose gel. Plasmid pQE30 (manufactured by Quiagene) also was digested by BamHI and SalI, and large fragment was eluted from the agarose gel to construct AK3 expression vector. Ligation of DNA fragments was done with the mixture of 3 µl of pQE30 large fragment, 5 µl of digested AK3 fragment, 1 µl of T4 DNA ligase and 1 µl of 10× ligase reaction buffer by incubation at the temperature of 16° C. overnight. For the host cell used in transformation, *E. coli* M15 was used. The colony obtained by plating on the plate containing ampicillin and kanamycin was incubated overnight in the LB culture medium. The plasmid was isolated and digested by EcoR1, and then the existence of insert was confirmed (refer to FIGS. 5 and 6). The colony wherein the insertion of the gene was confirmed, was incubated overnight in 50 ml of LB culture medium containing 100 µg/ml of ampicillin and 50 ml of the incubated product was inoculated in another LB culture medium of 1 L. After an hour of incubation at 37° C. with shaking, the growth of the recombinant bacilli was detected by 600 nm visible light absorbancy of 0.5 to 0.7 units. At this point of time, IPTG was added so as to be a final concentration of 1 mM and the expression of recombinant protein was induced for additional 4 hours of incubation. The induced broth was centrifuged at 4,000×g for 20 minutes to obtain cell pellets, and suspended in 50 ml of the buffer (binding buffer; 5 mM of imidazole, 0.5 M of NaCl, 20 mM of Tris/HCl containing 0.1% Tween 20, pH 7.9) and then maintained at the temperature of −20° C. The thawed suspension was applied to five times of 30 seconds ultrasonic disruption, following an one-minute pause cycle. The product was centrifuged at 10,000×g at the temperature of 4° C. for 30 minutes. The supernatant liquid was taken to obtain a crude extracts containing soluble proteins.

Figure 7A:
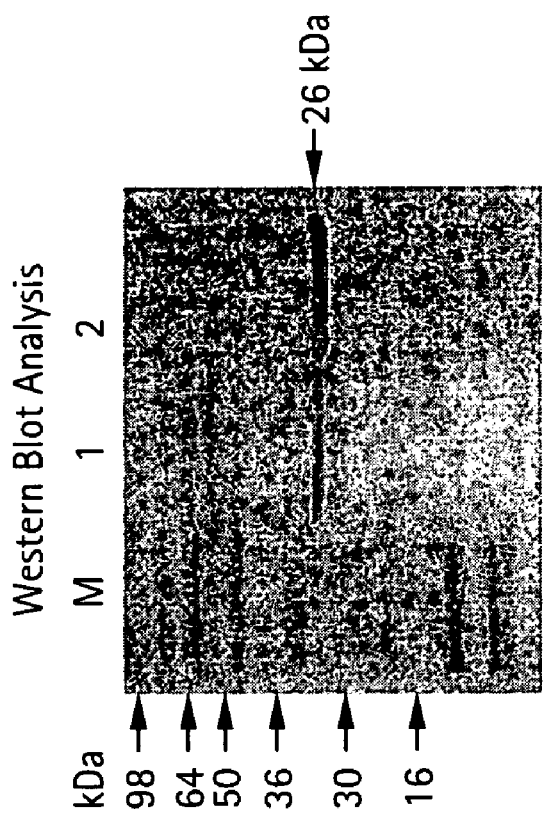
FIG. 7a is a drawing illustrating the result of the SDS-PAGE for AK3.
Figure 7B:
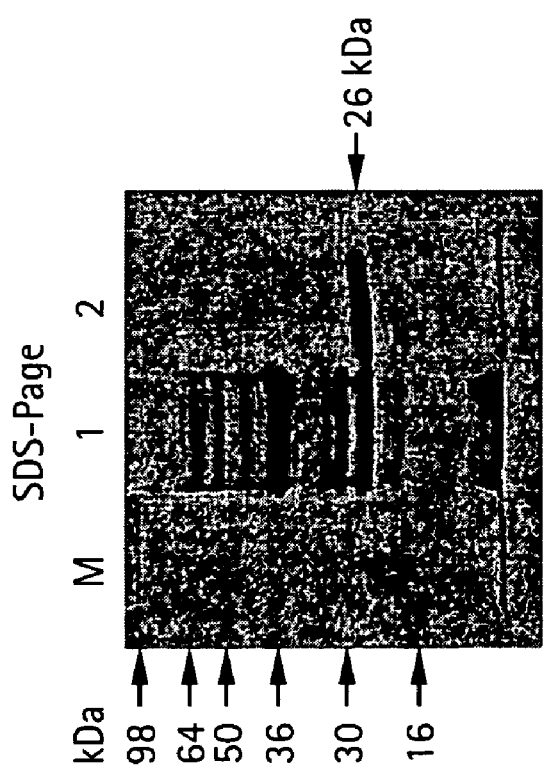
FIG. 7b is a drawing illustrating the result of Western blot analysis for AK3.

The expressed AK3 was purified by using a chelate resin (Pharmacia) which was packed in column for the bed volume to be 5 ml, was washed with distilled water by 5 column volume. Ethanol was removed, $Ni^+$ was bound to the chelate resin by using 5 column volume of charge buffer (50 mM of $NiSO_4$ containing 0.1% Tween 20), washed with distilled water of 3 column volume, and then equilibrated with the binding buffer of 5 column volume. The above-prepared crude extract was loaded, washed with the binding buffer of 10 column volumes, washed with washing buffer of 5 column volumes (20 mM Tris/HCl, pH7.9, containing 60 mM imidazole, 0.5 M NaCl and 0.1% Tween 20) to remove a nonspecific binding, and eluted with eluting buffer of 5 column volume (10 mM of Tris/HCl, pH7.9 containing 0.5 M of NaCl, 1 M imidazole and 0.1% Tween 20). At this time, the flow rate in all the steps was 1 ml/min. From the eluted AK3, the salts were removed in the dialysis buffer (10 mM Tris/HCl containing 0.1% Tween 20, pH 7.9) while exchanging the buffer three times for 12 hours, and then concentrated with PEG 8000. The concentration of the protein was quantitatively measured by using a BCA protein quantitative analysis kit, the calculated purification yields were listed in Table 1, and the purified AK3 was used in analysis of SDS-PAGE Assay (FIG. 7) or purification and production of antibody.

TABLE 1

(Purification Of Recombinant AK3)

| Purification Steps | Total Protein(mg) | Purification Yield (%) |
|---|---|---|
| Homogenate | 949.05 | 100 |
| Soluble Fraction | 178.75 | 18 |
| Ni-Chelate Affinitive Chromatography | 14.3 | 1.5 |

EXAMPLE 3

Production and Purification of Anti-AK3 Rabbit Antibody

One ml of the purified AK3 protein and 1 ml of Freund's complete adjuvant (FCA) were mixed by emulsifier syringe to give an emulsion. The emulsion was injected intravenously or intradermally to a NZW-rabbit (male) of 2 kg-body weight. For the first week, 50 to 100 µg/ml of antigen emulsion was prime-injected intradermally at several regions of the rabbit. From the next injection, 100 µg/ml of the antigen emulsified with Incomplete Freund's Adjuvant (IFA) was boosting-injected intradermally twice at intervals of every two weeks. One week later from the final inoculation, the blood was collected from the vein of the rabbit ear to detect an induction of antibody, and antibody production was detected by dot blotting analysis. For the fifth week, 100 µg of protein was injected intradermally. For the sixth week, the protein solution (20 µg/ml) mixed with no adjuvant was injected intravenously for boosting. And then, after fasting the rabbit for 24 hours, the blood was collected from the heart by cardiac puncture and from which serum was prepared.

The collected blood in a glass container was left at room temperature for 1 hour to be clotted, and was stood at the temperature of 4° C. for 6 hours. The clotted portion was removed by centrifuged at the temperature of 4° C. and 2,500×g for 30 minutes and the serum was isolated. Polyclonal anti-AK3 antibodies purified from the isolated serum was obtained by the below antibody purifying method to eliminate a cross-reactive antibodies with isozymes AK1 and AK2 having high homology with AK3. Each 500 μl of the serum aliquote was stored at the temperature of −80° C. and was used in biochemical analysis for screening the serum of the patient.

Figure 8A:
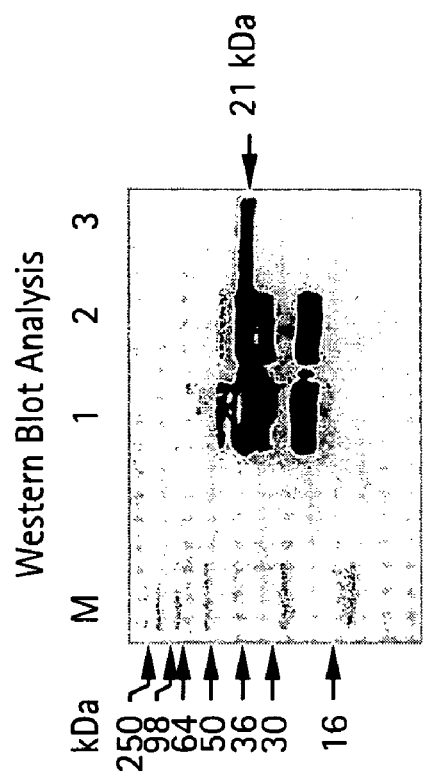
FIG. 8a is a drawing illustrating the result of the SDS-PAGE for AK1.
Figure 8B:
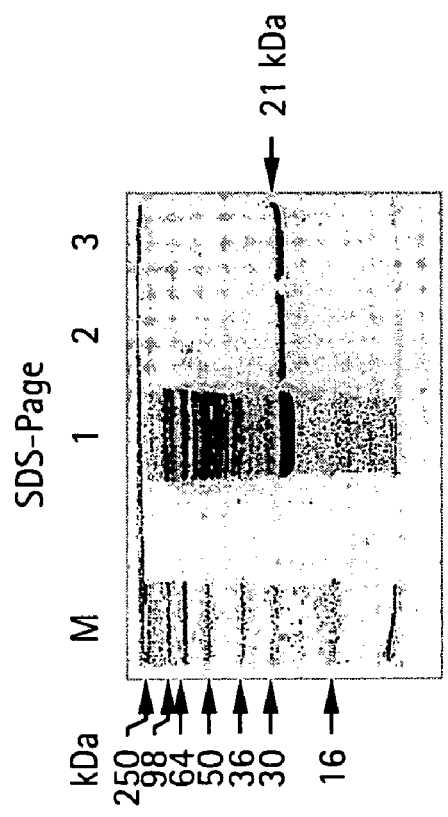
FIG. 8b is a drawing illustrating the result of Western blot analysis for AK1.
Figure 9B:
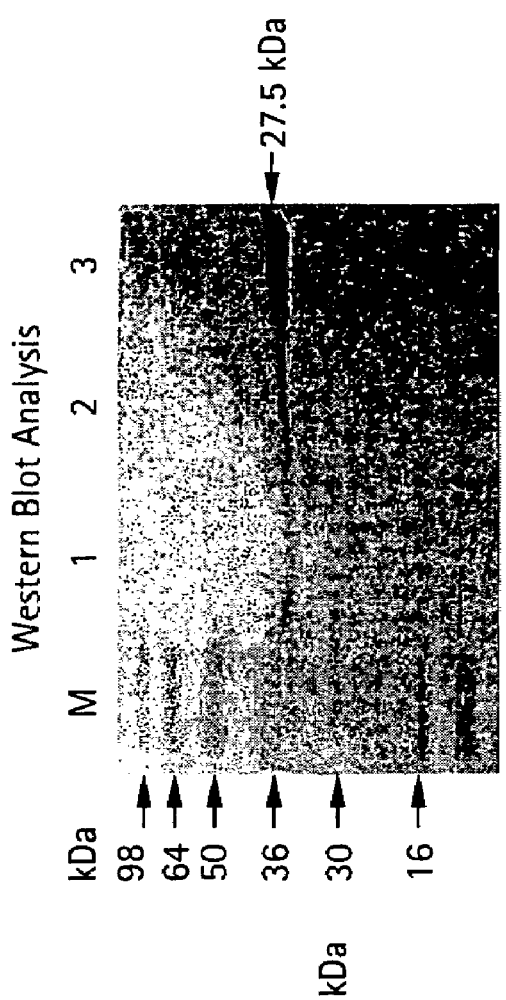
FIG. 9b is a drawing illustrating the result of Western blot analysis for AK2.
Figure 9A:
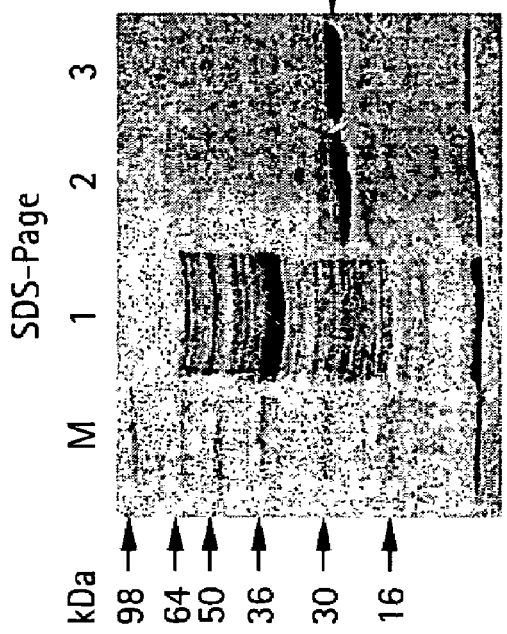
FIG. 9a is a drawing illustrating the result of the SDS-PAGE for AK2.
Figure 10:
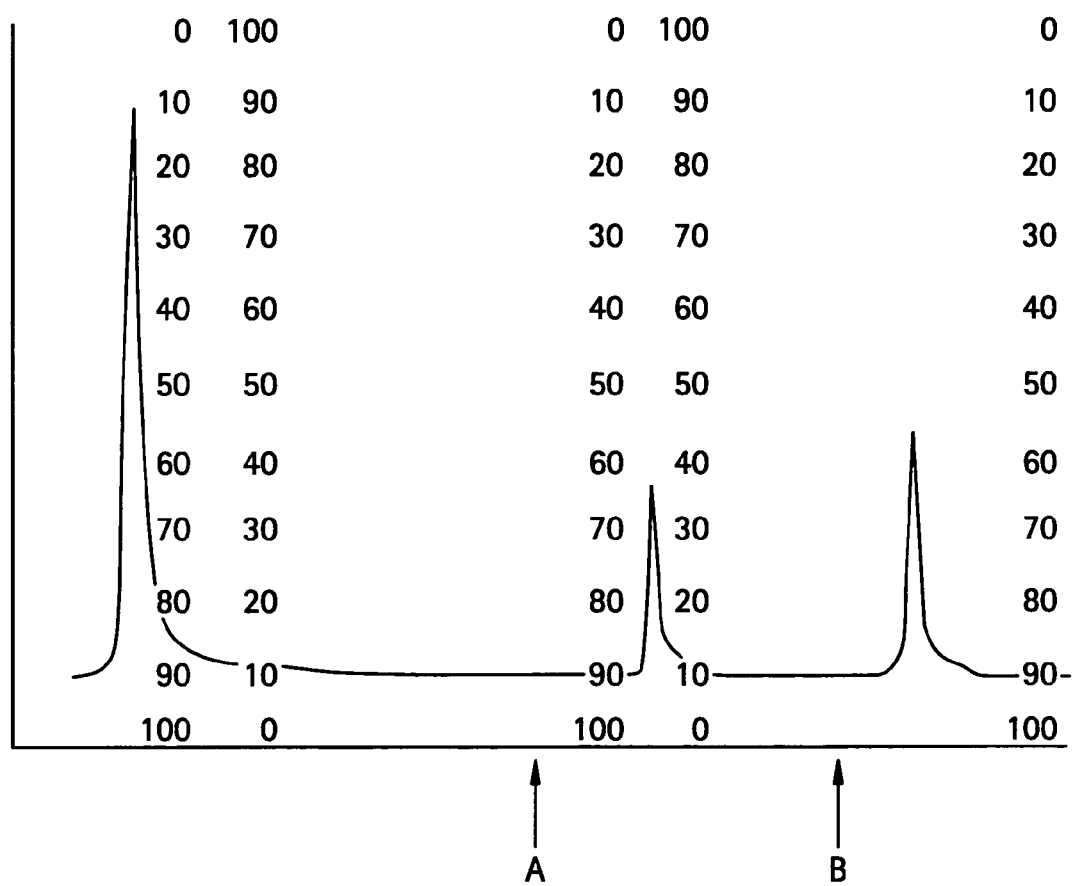
FIG. 10 is a graph illustrating a purification behavior of anti-AK3 rabbit antibody.
Figure 11:
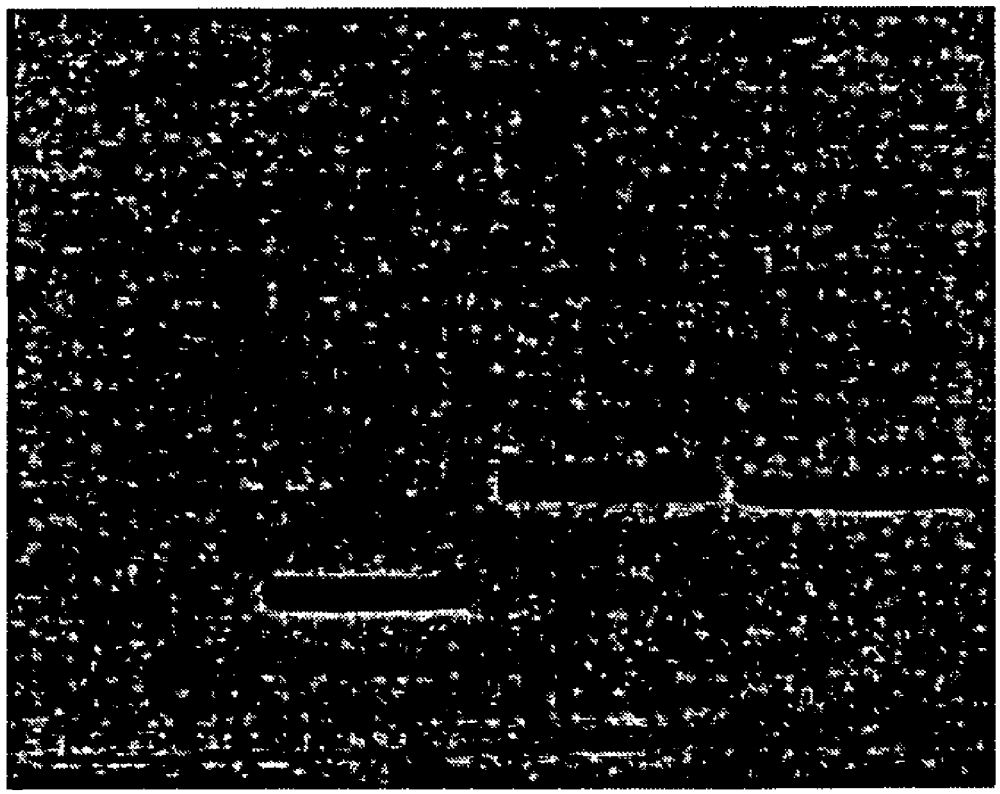
FIG. 11 is a drawing illustrating a purified recombinant of AK isozymes.

Anti-AK3 polyclonal antibody purification procedures are as follow. The isolated rabbit serum was applied onto a CM affi-gel blue affinitive chromatography which having a high antibody recovery rate. CM Affi-gel blue resin was washed with 0.1 M acetic acid (pH3.0) containing 1.4 M NaCl and 40% isopropanol and the secondary distilled water and packed into a glass column. And the column was equilibrated with PBS. The eluent of the entire peak that appeared for the first time after loading anti-serum on column was pooled. Immunoglobulins in the above eluent were precipitated by the ammonium sulfate precipitation under the condition of ammonium sulfate concentration of 45% saturation. In order to obtain the AK3-antibody having a AK3-specificity and no cross-reactivity with AK1 and AK2 among the said immune globulins, the purified AK1 (FIG. 8) and AK2 (FIG. 9) were coupled to affi-gel 15 (Bio-Rad), and AK3 was coupled to affi-gel 10 (Bio-Rad), to prepare are affinity column chromatography. The affinity chromatography columns loaded with AK1, AK2 and AK3, respectively were connected in order and equilibrated with 0.1 M sodium phosphate buffer (pH 7.5) containing 0.5 M NaCl. In order to remove nonspecifically binding antibodies, it was washed with 0.1 M sodium phosphate buffer (pH 7.5) containing 1 M KCl. Finally AK3 specific antibodies were eluted with 0.1 M glycin/HCl (pH 2.5) (refer to FIG. 10). The eluent was added directly into $\frac{1}{20}$ volume of 2 M Tris/HCl (pH 7.5) to neutralize the strong acidity. The above-purified AK3-specific polyclone antibody was dialyzed in PBS, stored at the temperature of 4° C. and was used in Western blot analysis. AK1, AK2 and AK3 antigens to the prepared adenylate kinase isozyme antibodies (anti-AK1 Ab, anti-AK2 Ab and anti-AK3 Ab) were subjected to Western blot analysis according to the below method and were confirmed to have no cross-reactivity with each other (refer to FIG. 11 and FIG. 12). In case of electrophoresis of the purified recombinant AK, a general SDS-PAGE of Lamile method was commenced and in case of nonsubstitution, a modified native gel electrophoresis was commenced. After completing SDS-PAGE of modified native gel electrophoresis, transfer gasket made in such an array wherein a fiber is placed on gel holder after completing SDS-PAGE or modified native gel electrophoresis, a filter paper is placed thereon, a PVDF film pretreated with ethanol is laid thereon, a gel is laid thereon and a fiber is covered thereon. The transfer sandwich was put in a buffer tank equipped with a cooling device, and the constant electricity (90 V, 0.8 A) was applied for 2 hours. PVDF film was taken from gel holder after detecting prestained marker's transfer, dipped into the TEST blocking solution containing 5% of nonfat dried milk and then slightly shaken for 2 minutes. Protein-blotted PVDF film was immersed into anti-AK3 antibody solution having an adequate concentration and then shaken at the room temperature for 1 hour. The antibody bound film was washed twice with TBST to remove the non-specifically bound antibodies. Washed PVDF membrane was treated with Horseradish peroxidase conjugated anti-rabbit antibody solution for 1 hour at 37° C. Membrane was then washed thoroughly with TBST. After completely removing TBST from the film, they were reacted by using ECL Western blot analysis kit, and then developed by exposing it to a X-ray film.

EXAMPLE 4

Detection of AK3 from Patient's Serum

From the tissue distribution of AK3 in skeletal muscle and cardiac muscle according to the Western blot analysis, it was confirmed that AK1 exists in both a skeletal muscle and a cardiac muscle, and AK2 and AK3 exist in only cardiac muscle (refer to FIG. 13). Because a cardiac tissue-specificity of AK2 and AK3 shows a possibility to be used as a biological marker which can diagnose a disease such as a myocardial infarction, it was confirmed whether or not AK2 and AK3 can be detected from a serum of a myocardial infarction-patient by Western blot analysis after electrophoresing them under the conditions of reducing and non-reducing, respectively (refer to FIG. 14). Thereby, the presence of AK2 and AK3 could not be confirmed according to. Western blot analysis under these conditions of substitution due to nonspecific binding with serum proteins. The presence of AK2 could not be confirmed according to Western blot analysis under the condition of SDS-PAGE. For AK3, the band could be confirmed from the myocardial infarction-patient's serum at the same region as the purified AK3 because of the overlapping with nonspecific bands. However, because many nonspecific bands were always detected, a new electrophoresis method which can detect only AK3 was developed. The new electrophoresis method is the one that the electricity is flown at the reverse direction which was different from a general direction when commencing a conventional acrylamide gel electrophoresis, wherein the native gel is consisted of 2 ml of monomer solution (40% T 5% Cbis), 2.5 ml of 4× isolation gel buffer (158 mM Tris, 0.256N $H_3PO_4$, pH6.9), 4.25 ml of $H_2O$, 1.25 ml of catalyst (0.06% ammonium sulfate, 0.02% riboflavin phosphate) and 20 μl of TEMED. The sample was loaded by mixing 1 μl of serum, 8 μl of DW and 1 μl of sample buffer (50% sucrose, 0.1% bromophenol blue), 20 mA of electricity was flown in the tank buffer (25 mM Tris, 55% glycin) for 2 hours with the reverse direction method.

Figure 15:
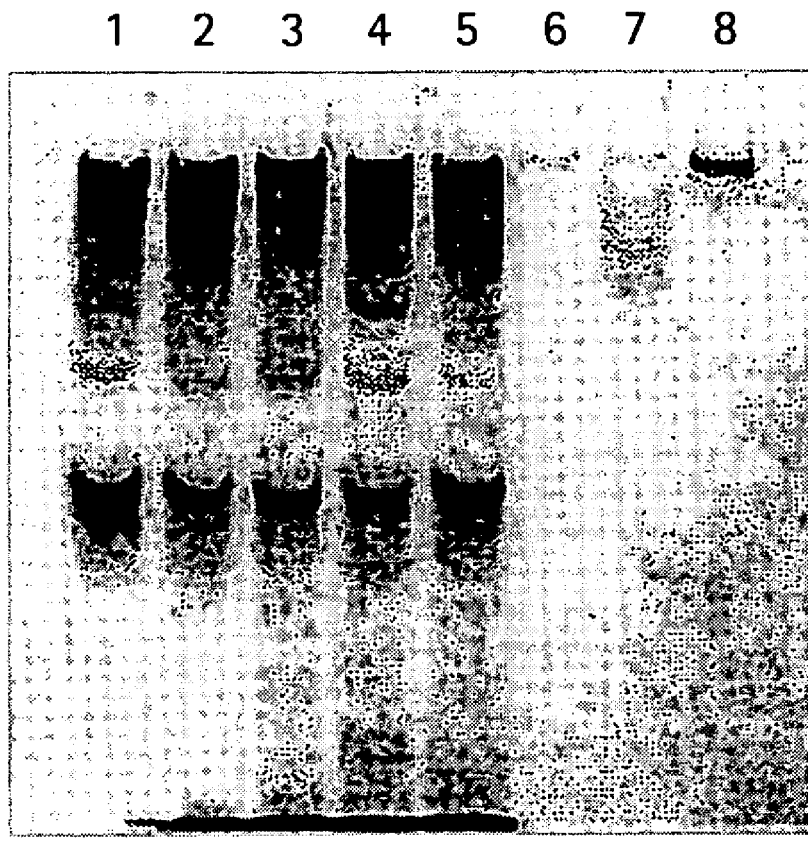
FIG. 15 is a drawing illustrating a migration pattern of native gel electrophoresis for AK and human serum.

Migration direction of AK1, AK2 and AK3 was identified by loading the purified AKs, the patient's serum and the normal serum on the gel according to the above-mentioned method. It was confirmed that the strongly basic AK3 was propagated into the gel, and that AK1 and AK2 were diffused into the tank buffer (refer to FIG. 15).

EXAMPLE 5

Production of Anti-AK2 and Anti-AK3 Monoclonal Antibodies

For anti-AK3 and anti-AK2 monoclonal antibodies, an emulsion(0.1 ml) obtained by mixing 50 μg of an antigen protein solution and the same volume of Freund complete adjuvants was primarily injected to both foot pads of 4 weeks-aged Balb/c (H-2d haplotype) mouse, and inoculated twice at an interval of 10 days, from the second injection for boosting, an immune adjuvant, the incomplete Freund's adjuvant was used. After confirming that the antibody was produced in the serum of the mouse, a lymph node was taken, a cell suspension was made with Dulbecco's Modified Eagle's Medium (DMEM) broth containing a fetal calf serum, IL-2, penicillin-streptomycin B lymphocytes in this cell suspension and the previously prepared Sp2/0-Ag14 myeloma cell line which is tumor cell of the same mouse strain as the above was fused by the PEG treatment. Each $1.5 \times 10^8$ cells of immune cells and Sp2 cells was taken, centrifuged in a centrifuge tube at 400×g for 10 minutes to form pellets, the supernatant was removed, 1 ml of 50% PEG 1500 at 37° C. was added thereto, mixed with the tip of the pipette for 1 minutes and stirred very carefully. One ml of the culture medium containing no fetal calf serum at 37° C. was added thereto for 1 minute, and a serum-free medium was continuously added thereto with stirring and gradually diluted for cells not to be dissolved by PEG. Finally, 7 ml of the serum-free medium was added thereto and stirred for about 3 minutes. After cells were washed, they were sufficiently dispersed by adding 20 ml of broth, each 0.1 ml of the dispersion was divided into 96-well tissues culture plates, and incubated in 7% $CO_2$ incubator at 37° C. for 24 hours to create a master plate. Hybrid cells were sorted by using a viability in Hypoxanthine-Aminopterin-Thymidine (HAT) medium. The next day from the cell-fusion, 0.1 ml of HAT medium per every well was added thereto. On the second, third, fifth, eighth and eleventh day, each one half of broth medium was aspirated, 0.1 ml of fresh HAT medium was partially changed. After that time, at the interval of 3 or 4 days the same procedure as the above was repeated, the wells harboring cells survived after 4 weeks were separately selected, their supernatant was taken, ELISA was conducted by using AK3-coated 96-well microtiter plate. In this analysis, only wells having 0.3 or more of absorbancy for light of 405 nm were selected by using 1 ml of culture. The selected cells were transferred to 24-well tissue culture plate, and were proliferated in 1 ml of scale with Balb/c-derived feeder cell (cell suspension treated with mitomycin after a red blood cell dissolution of splenial cells of Balb/c) in HT medium instead of HAT for 15 days by 2 ml and 10 ml of culture, respectively. In this process, cloning of hybridoma cell was attempted by a limiting dilution method. Thirty six wells were diluted in density of 5 cells/well, another 36 wells in density of 1 cell/well, and the remaining 24 wells in density of 0.5 cells/well in the 96-well micro-titer plate. Cell passing was conducted 5 days and 12 days later from incubation, and then proliferated as the above by 1 ml culture scale. The incubated supernatant of the well wherein a monoclonal antibody is appeared to be derived, was selected, and ELISA for antibody screen was conducted. In this process, the clones indicating cross-reactivity with AK1 and AK2 were removed, and the hybridoma cells specifically recognizing only AK3 were strictly selected and classified as an anti-AK3 monoclonal-producing cell lines. Finally selected hybridoma was transferred to 5 ml-incubation flask and prolifically incubated. For production of monoclonal antibody (mAb) from the created cell line, the hybridoma cells were cultured in RPMI 1640 with supplements (10% Fetal bovine serum, HAT, penicillin and G418) which sereted mAb into the culture medium. Monoclonal antibody was isolated and purified (25 µg antibody per ml culture) from the culture medium. Alternatively, mAb was induced from murine ascites. Hybridoma cells were cultured in the presence of 5% carbon dioxide in DMEM broth, 3 days later $2 \times 10^6$ fusion cells in a healthy state were harvested and injected intraperitonealy into a Balb/c mouse to cause tumor proliferation and derive antibody from the ascites. The antibody was isolated and purified by AK3 affinity column chromatography in yield of 0.8 mg/ml.

EXAMPLE 6

Diagnosis for Myocardial Infarction using AK3 Antibody and Usage of AK3 as Biochemical Marker for Myocardial Infarction Referring to FIG. 13, the expression aspect of AK3 for muscular tissues was specific to a cardiac muscle. Considering a possibility for AK3 to be released in blood due to an injury of a cardiac muscle, in this example, an experiment was conducted for usage of AK3 as an diagnosis indicator for a myocardial infarction by using a serum sample collected from the outpatient in an emergency room of a general hospital.

30 individuals of serum sample were used, and the names of diseases were indicated in Table 2. Among 5 myocardial infarction patients, the acute patients are 4 persons and the chronicle patient is one person. CKMB unit of each serum was detected in a clinical pathology laboratory. CKMB unit of the healthy person was below 7 which is referred to as normal.

The sera of 29 patients were tested as the above by Western blot analysis using anti-AK3 antibody. At the result, for the myocardial infarction patient, AK3 was detected with being identical to the concentration of CKMB (refer to FIG. 16). However, for the patient having an operation for leg bone fracture, CKMB was 44 units and false positive, but AK3 was not detected (refer to FIG. 16, panel B, lane 8). For the patient underwent an operation for cerebral hemorrhage (patient No. 22 in Table 2), CKMB numeral was very high as much as 56.3, but a heart abnormality was not detected. In this example, AK3 was not detected. The result of this experiment proves that the detection of AK3 using anti-AK3 antibody is more correct diagnosis for myocardial infraction than CKMB. Accordingly, in diagnosis for acute or chronicle myocardial infraction, an immunological formulation or a diagnostic kit using anti-AK3 antibody was more correct than diagnosis using myoglobulin of CKMB. Accordingly, it was apparent that a diagnostic kit using the antibody according to the present invention was clinically myocardial-specific.

TABLE 2

| Patient's No. | Names of Diseases | Sex/age | Numerals of CKMB | AK3 detection |
|---|---|---|---|---|
| 0 | Normal control serum | M/26 | | − |
| 1 | Stable angina | M/62 | 2.7 | − |
| 2 | Unstable angina | M/53 | 4.6 | − |
| 3 | Peritonitis operation | M/54 | 7.3 | − |
| 4 | Acute myocardial infarction | M/56 | 22.1 | + |
| 5 | Typhlitis operation | F/32 | 3.0 | − |
| 6 | Atrial fibrillation | M/45 | 3.3 | − |
| 7 | Ischemic myocardial Disease (person having anamnesis of myocardial infarction) | M/78 | 2.8 | − |
| 8 | Esophageal cancer | M/55 | 1.1 | − |
| 9 | Leg bone fracture operation | M/25 | 44.0 | − |
| 10 | Unstable angina | M/67 | 3.6 | − |
| 11 | Interventricular | M/34 | 8.5 | − |
| 12 | Asthma | M/76 | 9.2 | − |
| 13 | Acute myocardial | M/40 | 40.4 | + |
| 14 | Unstable angina | M/67 | 2.5 | − |
| 15 | Unstable angina | M/58 | 5.8 | − |

TABLE 2-continued

| Patient's No. | Names of Diseases | Sex/age | Numerals of CKMB | AK3 detection |
|---|---|---|---|---|
| 16 | Interventricular | M/34 | 12.8 | − |
| 17 | Peritonitis | M/85 | 5.6 | − |
| 18 | Myocardial | M/41 | 18.0 | + |
| 19 | Myasthenia gravis | F/45 | 6.2 | − |
| 20 | Unstable angina | M/67 | 0.7 | − |
| 21 | Lung cancer | M/79 | 2.7 | − |
| 22 | Cerebral hemorrhage | M/25 | 56.3 | − |
| 23 | Intestine burst | M/64 | 4.3 | − |
| 24 | Myocardial | M/67 | 2.9 | − |
| 25 | Dysrhythmia | F/52 | 2.7 | − |
| 26 | Multiple rib | M/18 | 3.9 | − |
| 27 | Diabetes, | F/91 | 2.4 | − |
| 28 | Somatization | M/28 | 3.1 | − |
| 29 | Acute myocardial | M/34 | 56.3 | + |

Figure 16B:
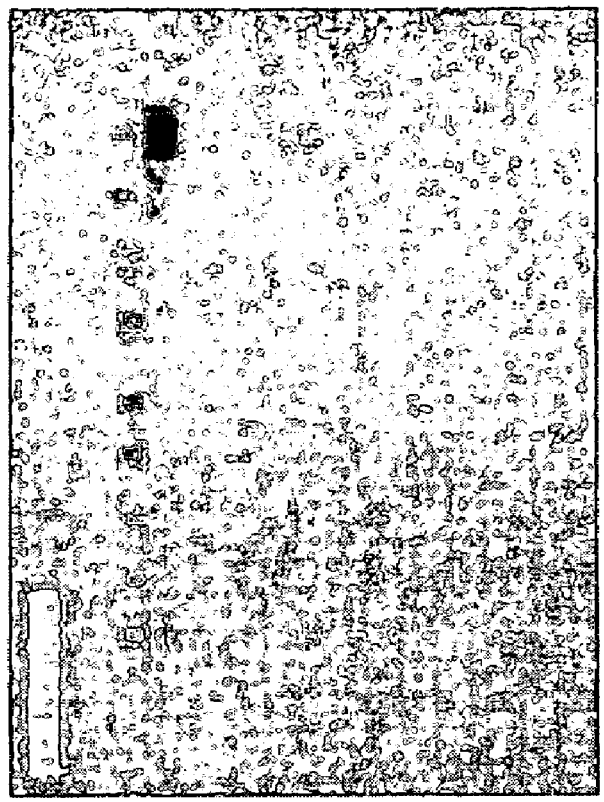
FIG. 16 is a drawing illustrating the result of Western blot analysis for detecting AK3 in the patient's serum.
Figure 16A:
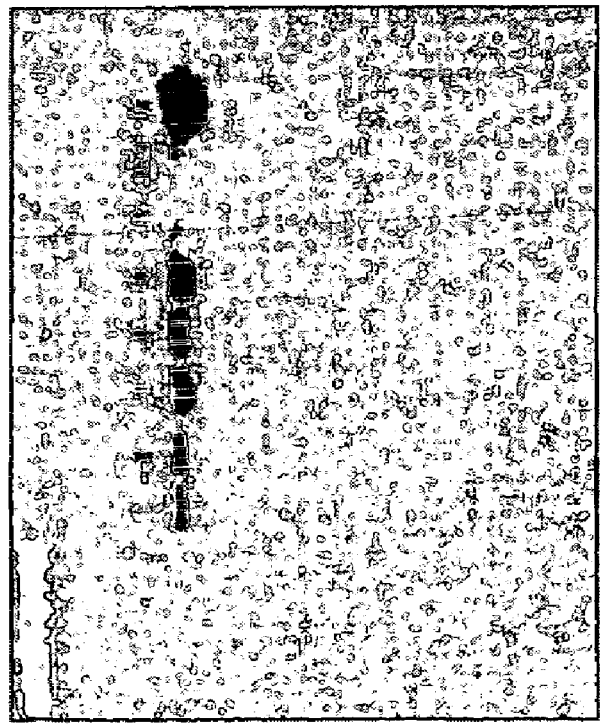

FIG. 16 is a drawing showing the result of Western blot analysis for detecting AK3 in a patient's serum. The information for the test serum in FIG. 16 was provided in below Tables 3 and 4.

TABLE 3

[Information on Test Serum of FIG. 16 (Statement of Panel A)]

| Lane No. | Names of Diseases | CKMH Unit[a] | Patient's No. in Table 2 |
|---|---|---|---|
| 1 | Acute myocardial infarction | 22.1 | 4 |
| 2 | Acute myocardial infarction | 40.4 | 13 |
| 3 | Acute myocardial infarction | 18 | 18 |
| 4 | Acute myocardial infarction | 56.3 | 29 |
| S | Human cardiac tissue sample | | |
| N | Normal serum | | |
| Ak2 | Purified recombinant AK2 | | |
| p | Purified recombinant AK3 | | |

[a]CKMB of the normal serum was less than 7 units.

TABLE 4

(Information on Test Serum of FIG. 16 (Statement of Panel B)]

| Lane No. | Name of Disease | CKMB Unit | Patient's No. in Table 2 |
|---|---|---|---|
| 5 | Stable angina | 2.7 | 1 |
| 6 | Esophageal cancer | 1.1 | 8 |
| 7 | Atrial fibrillation | 3.3 | 6 |
| 8 | Leg bone fracture | 44.0 | 9 |
| 9 | Interventricular septal defect operation | 12.8 | 16 |
| 10 | Peritonitis operation | 5.6 | 17 |
| 11 | Lung cancer | 2.7 | 21 |
| N | Normal serum | n.d.[a] | |
| P | AK3 | | |

[a]n.d.; not determined

EXAMPLE 7

Diagnosis for Myocardial Infarction using AK3 Antibody and Clinical Specificity Test for Myocardial Infarction In this experiment, in order to confirm a clinical specificity of AK3 as a biochemical marker for diagnosing a cardiac disease, the test sera were collected from the inpatients who were admitted to the circulatory internal medicine of Guro general hospital affiliated in Korea University and were definitely diagnosed as a myocardial infarction. A concentration of CKMB was measured, and ECL-Western blot analysis and Sandwich ELISA against AK3 were conducted.

According to the ELISA, the affinity-purified rabbit anti-AK3 polyclonal antibody (450 ng/well) was attached to the 96-well microtiter plate, 100 μl of serum was added thereto and reacted at the temperature of 30° C. for 1 hour. The reactant was sufficiently washed with phosphoric buffered physiological saline (PBS), was secondarily reacted with the biotinylated rabbit anti-AK3 polyclonal antibody, was treated for binding HRP fused with streptoavidin and treated for chromophore substrate. And then, light-absorbancy was determined by ELISA detector. In this experiment, as a standard material the genetic recombinant AK3 isolated and purified by the present inventors was used. The diagnostic results for acute myocardial infarction (AMI) using CKMB and AK3 antibody were shown in below Table 5.

TABLE 5

| | | | AK3 | | |
|---|---|---|---|---|---|
| Sample ID | Names of diseases | CKMB[a] (ng/ml) | Western[a] blot Analysis | Sandwich ELISA[a] (μg/ml) | Remarks (age/sex) |
| 1 | 417 Myocardial infarction | 406.6 | ++ | 2.0 | 75/M |
| 2 | 436 Myocardial infarction | 123.8 | ++ | 10.0 | 58/M |
| 3 | 464 Myocardial infarction | 230.9 | +++ | 4.7 | 67/M |
| 4 | 474 Myocardial infarction | 47.23 | ++ | 11.6 | 65/M |
| 5 | 481 Myocardial infarction | 378.6 | + | 2.0 | 53/M |
| 6 | 487 Myocardial infarction | | + | 3.0 | |
| 7 | 503 Myocardial infarction | 51.1 | + | 7.3 | 56/M |
| 8 | 514 Myocardial infarction | 33.2 | ++ | 7.6 | 53/M |
| 9 | 526 Myocardial infarction | 2.15 | ++ | 3.3 | 57/F |
| 10 | 547 Myocardial infarction | 314.2 | +++ | 7.0 | 60/M |
| 11 | 548 Myocardial infarction | 71.79 | + | 4.2 | 63/M |
| 12 | 553 Myocardial infarction | 175.4 | +++ | 5.8 | 52/M |
| 13 | 565(6) Myocardial infarction | >500.0 | +++ | 4.7 | 61/M |
| 14 | 578 Myocardial infarction | 176.7 | + | 8.1 | 57/M |
| 15 | 606 | 1.55 | + | 1.2 | 64/M |
| 16 | 607 | | +++ | 10.0 | |
| 17 | 614 | 19.84 | + | n.d.[c] | 62/M |
| 18 | 616 | 97.93 | ++ | n.d. | 45/M |
| 19 | 621 | 1.79 | + | n.d. | 66/M |
| 20 | 625 | 1.85 | + | n.d. | 51/M |
| 21 | 626 | 1.62 | ++ | 5.0 | 41/M |

[a]CKMB analysis was conducted in Ansan general hospital affiliated in Korea University.
[b]Light-absorbancy for serum of the healthy person in sandwich ELISA: $A_{490}$ <0.02 in cases of all of 6 samples separated from healthy persons showed the values under the reference range.
[c]The test was not conducted due to lack of serum.
[d]All are AK3-positive.

Figure 17A:
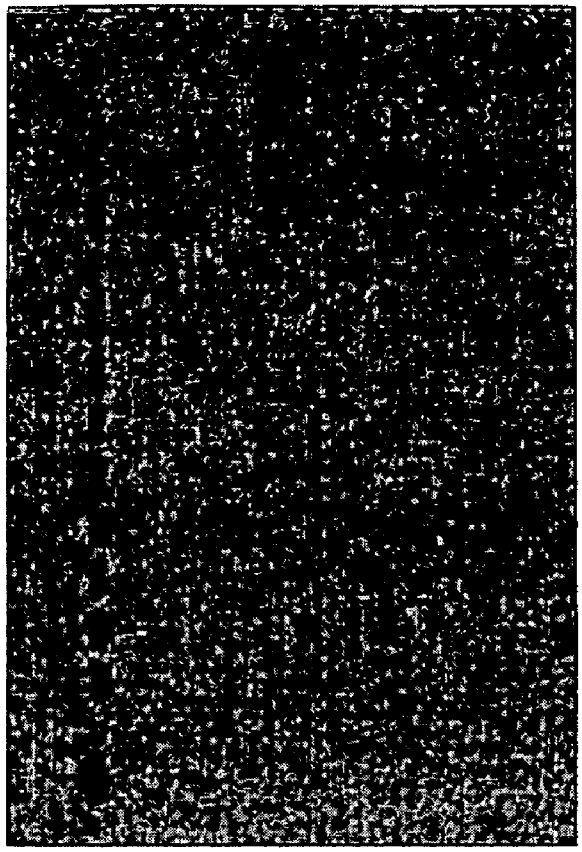
FIG. 17 is a drawing illustrating the result of Western blot analysis for AK3 in Example 6.
Figure 17B:
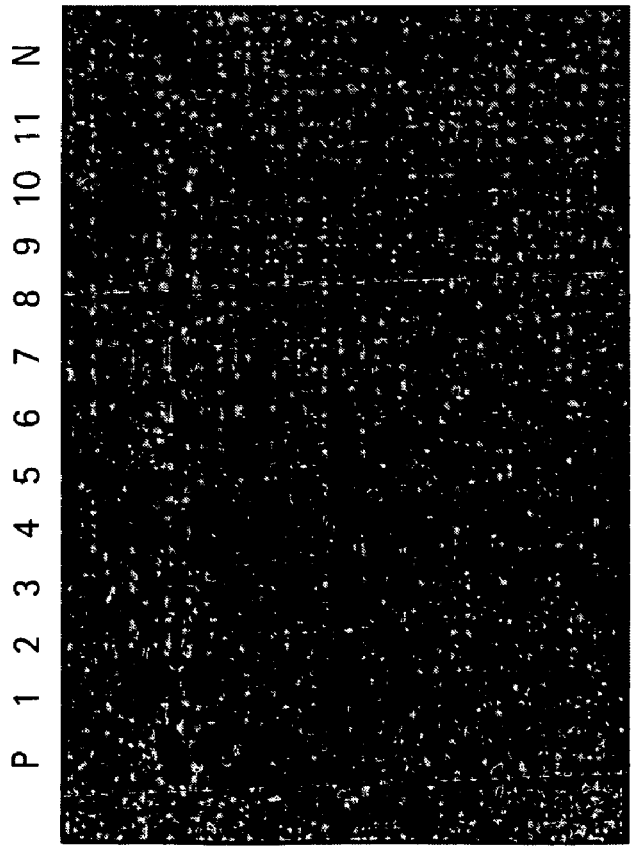

FIG. 17a and FIG. 17b show the results of AK3 Western blot analysis using ECL substrate.

As seen from the above Table 5, from the diagnostic indicator analysis for CKMB and AK3 using the serum samples collected from the total 60 patients including 21 samples collected from the patents who were definitely diagnosed as a myocardial infarction in the circulatory internal medicine of Guro general hospital affiliated in Korea University and 10 samples collected from the myocardial infarction patients admitted to the general hospital affiliated in Hanyang University in Korea, it was confirmed that AK3 was detected with 100% accuracy. Even all the patients who were diagnosed as falsely negative in CKMB test being used now as an representative optimal indicator for a diagnosis of myocardial infarction could be decided to be positive by AK3 analysis. Therefore, the immunological- formulation according to the present invention is more accurate in diagnosis as well as has a high specificity to pathological-biological analysis and a high clinical specificity.

INDUSTRIAL APPLICABILITY

As apparent from the above description, the human mitochondria adenylate kinase isozymes, especially AK3 to be distinctively used in the present invention has the following features:

tion analysis easy. Moreover, the analyzing samples are stable and cheap, and have no disturbance and interference. They have also more correct accuracy than a conventional standard diagnostic indicator of CKMB, which is predominantly used in a clinical pathology. In addition, the diagnostic kit according to the present invention can be applied to both patch-type and strip-type kits, and thus provides a fast and simple diagnosis. As the prior diagnostic methods require an expensive equipment and a high level of diagnostic techniques, or POCT rapid kits requires multiple markers to be tested simultaneously with several repeated tests at a expensive costs, they can be commenced only in a limited few general hospitals, meanwhile the diagnostic kit according to the present invention is cheap and can be easily used even in a small hospital and by an individual. Further, an import saving effect for the expensive foreign diagnostic reagents and kits can be expected.

```
SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
ggatccatgg cttccaaact cctgc                                          25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
cagggtcaat atgcttcttt gg                                             22
```

(1) it is released to the circulatory blood by the cardiac muscle-specific injury;

(2) it released immediately upon the cardiac muscle injury;

(3) as it has a substantial life time in circulation, the continuous increasing numerals show the continuity of a cardiac muscular injury (in case of sample No. 7 of Table 2, AK3 was not detected in serum of the person having anamnesis of myocardial infarction). Thus abnormal pathologic concentrations of AK3 vs time after onset of AMI showed linear relationship; and (4) a serum concentration increase is confirmed within 2 hours after a chest pain initiates (FIG. 16, Lane 3).

Accordingly, the immunological formulation or diagnostic kit according to the present invention makes possible early diagnosis for a cardiac disease such as a myocardial infarction; does not require a special technique or training to obtain the result of a suitable clinical analysis; and makes automa-

The invention claimed is:

1. A method for diagnosing myocardial infarction in a subject which comprises:
   (i) producing an immune complex by contacting an antibody or a portion thereof which binds to human mitochondrial adenylate kinase isozyme 3 (AK3) with a biological sample from said subject and a normal control subject, respectively,
   (ii) detecting the immune complex obtained in step (i),
   (iii) comparing the detected results, and
   (iv) determining said subject has myocardial infarction when the detected amount of immune complex in the biological sample from said subject is greater than the detected amount of immune complex in the normal control subject.

2. The method for diagnosing according to claim 1, wherein the biological sample is selected from the group consisting of urine, blood, serum and blood plasma.

* * * * *